United States Patent [19]
Cardin et al.

[11] Patent Number: 5,512,177
[45] Date of Patent: Apr. 30, 1996

[54] NARROW POLY- AND MONO-DISPERSED ANOINIC OLIGOMERS, AND THEIR USES, FORMULATIONS AND PROCESS

[75] Inventors: Alan D. Cardin, Cincinnati, Ohio; Michael J. Mullins, Midland, Mich.; William A. Fordyce, Midland, Mich.; Thomas A. Chamberlin, Midland, Mich.; Michael J. Fazio, Midland, Mich.

[73] Assignees: The Dow Chemical Co., Midland, Mich.; Merrell Dow Pharmaceuticals Inc., Cincinnati, Ohio

[21] Appl. No.: 156,329

[22] Filed: Nov. 22, 1993

Related U.S. Application Data

[63] Continuation of Ser. No. 818,753, Jan. 9, 1992, Pat. No. 5,424,063.
[51] Int. Cl.[6] .............................. B01D 15/08; B07C 9/00
[52] U.S. Cl. ...................... 210/635; 210/198.2; 210/656; 210/723
[58] Field of Search .......................... 514/772.3; 521/28; 210/635, 656, 75, 198.2

[56] References Cited

U.S. PATENT DOCUMENTS

| | | | |
|---|---|---|---|
| 3,528,949 | 9/1950 | Rutledge | 528/367 |
| 3,833,744 | 5/1958 | Neher | 528/372 |
| 4,107,202 | 8/1978 | Conrow et al. | 562/49 |
| 4,312,855 | 6/1982 | Grand | 514/180 |
| 4,824,916 | 4/1987 | Kershner et al. | 525/420 |
| 4,895,660 | 6/1990 | Kershner et al. | 210/640 |
| 5,276,182 | 1/1994 | Cardin et al. | 564/49 |

OTHER PUBLICATIONS

Antiviral Research, 18 (1992), Mohan et al pp. 139–150.
Protein Purification, 2d Ed., *Separation in Solution*, 1987, pp. 186–215.
Polymer Fractionation, Academic Press, 1967, Manfred J. R. Cantow, Ed., pp. 43–67.
Polymer Fractionation, Academic Press, 1967, Manfred J. R. Cantow, Ed., pp. 462.
Dowex: Ion Exchange 1958, The Dow Chemical Co., Lakeside Press, pp. 39–66.
Journal of Chromatography Library, V. 41A, 1988, A127–A344.

*Primary Examiner*—Peter F. Kulkosky
*Attorney, Agent, or Firm*—Craig G. Svoboda; Karen L. Kimble

[57] ABSTRACT

The narrow poly- or mono-dispersed oligomers of the present invention are polyureas, polycarbonates, polyesters or polyamides having a recurring unit of from 3 to 50. These oligomers are water-soluble, preferably have a rigid backbone, have recurring units coupled by carbonyl linking moities which have anionic groups, display predominantly linear geometry such that regular spacing between anionic groups exists in an aqueous medium, and are pharmaceutically-acceptable. The narrow poly- or mono-dispersed oligomers are useful for the treatment and/or diagnosis of AIDS and/or ARC or HSV.

22 Claims, 9 Drawing Sheets

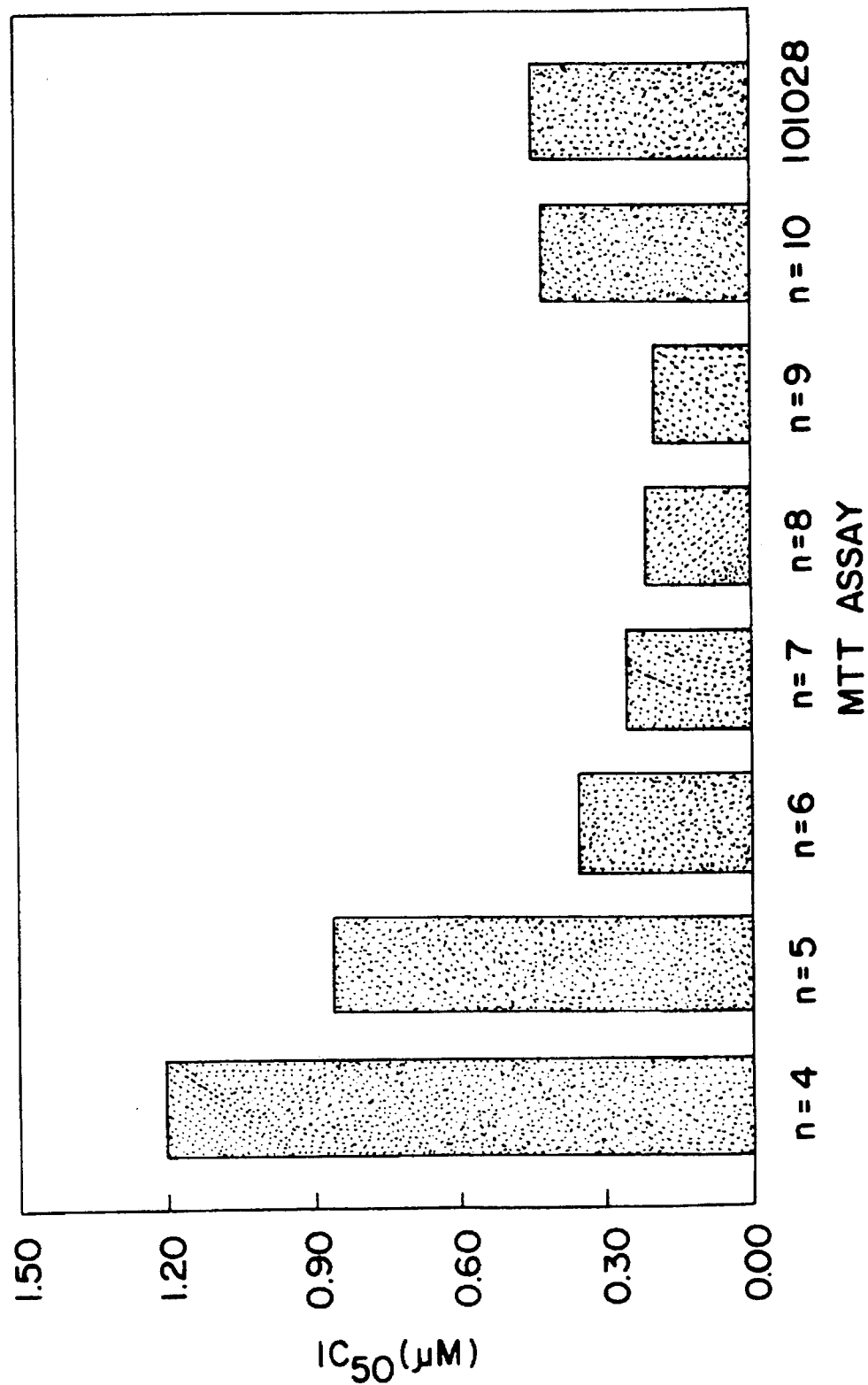

NARROW POLY- AND MONO-DISPERSED ANOINIC OLIGOMERS, AND THEIR USES, FORMULATIONS AND PROCESS

CROSS REFERENCE TO RELATED APPLICATIONS

This is a continuation filed under 37 C.F.R. § 1.60 of U.S. Ser. No. 07/818,753 filed Jan. 9, 1992, now U.S. Pat. No. 5,424,063, issued Jun. 13, 1995, and herein incorporated by reference.

The present invention concerns narrow poly- and monodispersed anionic oligomers, their preparation, formulations and use as valuable anti-human immunodeficiency virus activity agents. These monodispersed anionic oligomers are thus useful in the treatment of acquired immune deficiency syndrome (AIDS) and in the treatment of diseases caused by Herpes Simplex Virus (HSV) Types 1 and 2 and by Cytomegalovirus.

BACKGROUND OF THE INVENTION

A great deal of research is currently underway to develop treatments and cures for viral infections in humans and in animals, especially for Herpes Simplex Virus (HSV) Types 1 and 2 and AIDS and AIDS related complex (ARC). Notably the incidence of AIDS and ARC in humans is increasing at an alarming rate. The five year survival rate for those with AIDS is dispiriting and AIDS patients, whose immune systems have been seriously impaired by the infection, suffer from numerous opportunistic infections including *Kaposi's sarcoma* and *Pneumocystis carninii pneumonia*. No cure for AIDS is known and current treatments are largely without adequate proof of efficacy and have numerous untoward side effects. Fear of the disease has resulted in social ostracism of and discrimination against those having or suspected of having the disease.

Retroviruses are a class of ribonucleic acid (RNA) viruses that replicate by using reverse transcriptase to form a strand of complementary DNA (cDNA) from which a double stranded, proviral DNA is produced. This proviral DNA is then randomly incorporated into the chromosomal DNA of the host cell making possible viral replication by later translation of viral message from the integrated viral genome.

Many of the known retroviruses are oncogenic or tumor causing. Indeed, the first two human retroviruses discovered, denoted human T-cell leukemia viruses I and II or HTLV-I and II, were found to cause rare leukemias in humans after infection of T-lymphocytes. The third such human virus to be discovered, HTLV-III, now referred to as HIV, was found to cause cell death after infection of T-lymphocytes and has been identified as the causative agent of AIDS and ARC.

The envelope protein of HIV is a 160 kDa glycoprotein. The protein is cleaved by a protease to give a 120 kDa external protein, gp120, and a transmembrane glycoprotein, gp41. The gp120 protein contains the amino acid sequence that recognizes the CD4 antigen on human T-helper (T4) cells.

One approach being explored is to prevent the binding of HIV to its target, the T4 cells in humans. These T4 cells have a specific region, a CD4 antigen, which interacts with gp120. If this interaction can be disrupted, the host cell infection can be inhibited.

Interference with the formation of the viral envelope glyoprotein could prevent the initial virus-host cell interaction or subsequent fusion or could prevent viral duplication by preventing the construction of the proper glycoprotein required for the completion of the viral membrane. It has been reported [See H. A. Blough et al., *Biochem. Biophys. Res. Comm.* 141(1), 33–38 (1986)] that the nonspecific glycosylation inhibitors 2-deoxy-D-glucose and β-hydroxynorvaline inhibit expression of HIV glycoproteins and block the formation of syncytia. Viral multiplication of HIV-infected cells treated with these agents is stopped, presumably because of the unavailability of glycoprotein required for the viral membrane formation. In another report [W. McDowell et al., *Biochemistry* 24(27), 8145–52 (1985)], the glycosylation inhibitor 2-deoxy-2-fluoro-D-mannose was found to inhibit antiviral activity against influenza infected cells by preventing the glycosylation of viral membrane protein. This report also studied the antiviral activity of 2-deoxyglucose and 2-deoxy-2-fluoroglucose and found that each inhibited viral protein glycosylation by a different mechanism. However, other known glycosylation inhibitors have been shown to have no antiviral activity. Thus the antiviral activity against viruses in general, and the viral activity specifically, of glycosylation inhibitors is quite unpredictable.

Research worldwide is currently underway to develop treatments and cures for HSV Types 1 and 2. Both HSV Types 1 and 2 show a predilection for infection of the ectodermal tissues wherein such infections by the virus cause lesions in the skin, oral cavity, vagina, conjunctiva, and the nervous system. Generally, infection by HSV Type 1 (HSV1) is associated with oral, facial and ocular lesions. Infection by HSV Type 2 (HSV2) generally results in genital and anal lesions. HSV infections left untreated often lead to blindness, neonatal deaths, and encephalitis. HSV Type 2 infections are at an epidemic levels in the US from venereal transmission. Greater than some twenty million persons are presently afflicted with the disease in this country with new cases and recurrences exceeding half a million annually. The annual cost of HSV infections results in a substantial economic loss to diagnose and treat. Epidemiological control of HSV is poor because the majority of the population, up to 90%, has been exposed to the virus.

Man serves as the natural host for HSV Types 1 and 2 infections whereby the virus is transmitted during close personal contact. Initial or primary infections by HSV Types 1 and 2 are contracted through breaks in the mucus membrane. In the healthy carrier the virus can be isolated in the tears, saliva, vaginal and other secretions, even during the absence of overt disease. From the mucus membrane they are able to replicate and spread to the regional lymph nodes. Occasionally these viruses can infect cells of the haemopoietic system and cause viremia.

Part of the difficulty in treating HSV infections results from the ability of these viruses to persist in a latent, or quiescent form. When the primary infection subsides or recedes, the virus generally resides in a latent form in the sensory nerve ganglia which innervate the site of primary infection. In ocular or oral infections with HSV Type 1, the virus generally resides in the trigeminal ganglia. In HSV Type 2 the virus generally resides in the sacral ganglia serving the genitalia and lower abdoman. The determinative period of latency of the HSV virus is unknown, other than this period can be upset by heat, cold, sunlight, hormonal and emotional disturbances, or by immunosuppressive agents, resulting generally in a recurrent infection.

Treatment of HSV infections have largely been ineffective. A number of strategies to stop the virus have been developed. These agents generally inhibit any one of a number of specific vital functions such as (1) adsorption, (2)

uncoating, (3) transcription, (4) protein synthesis, (5) nucleic acid replication, (6) maturation, and (7) release.

Most of the antiviral agents thus far used to treat HSV infections have been compounds that interfere with viral DNA. These compounds include Idoxuridine, Cytosine Arabinoside, Adenine Arabinoside, and Trifluorothymidine. Such agents also interfere with similar host functions which results in general problems with cell toxicity and systemic use in humans. Presently, acyclovir is the preferred medication to treat infections with HSV1 and HSV2 due to its potent antiviral effect and negligable toxicity. Poor solubility at high dosage and the emergence of drug-resistant viruses, however, limit the use of this drug.

A number of RNA and DNA containing viruses have envelopes into which virus-coded glycopeptides are incorporated. HSV and cytomegalovirus (CMV) are two such enveloped viruses. Infection of a hose cell by enveloped viruses initially relies on the interaction of various receptors on the host cell surface with the envelope glycoproteins of the viral membrane. Subsequently the virus and cell membranes fuse and the virion contents are released into the host cell cytoplasm. The glycoprotein containing envelope of the virus plays an important role in both the initial interaction of the virion and the host cell and in the later fusion of the viral and host cell membranes. The viral envelope seems to be derived from the cellular membrane, but the specificity is due to the viral encoded glycopeptides. Therefore, an inhibitor capable of interfering with the formation of the virus-specific membranes may prevent formation of infectious progeny virus.

It has been disclosed in U.S. application Ser. No. 295,856, filed Jan. 11, 1989 pending, that a purified form of heparin, a sulfated polysaccharide, binds through interactions to a viral protein which is responsible for cell recognition and provides limited inhibition of host cell infection. However, heparin causes some side effects, notably hemorrhage and increased clot formation time as well as thrombocytopenia. Use of heparin is contraindicated in patients who are actively bleeding, or have hemophilia, purpura, thrombocytopenia, intracranial hemorrhage, bacterial endocarditis, active tuberculosis, increased capillary permeability, ulcerative lesions of the gastrointestinal tract, severe hypertension, threatened abortion or visceral carcinoma. The contraindication for use by hemophiliacs is particularly of concern because many such individuals are now HIV positive.

It has long been recognized that certain synthetic, water-soluble polymers exhibit a broad spectrum of biological activity [R. M. Ottenbrite in "Biological Activities of Polymers", *Amer. Chem. Soc. Symp.* Ser. No. 182, pp. 205–220, eds. C. E. Carraher and C. G. Gebelein (1982)]. A copolymer of divinyl ether and maleic anhydride has been shown to be active against a number of viruses and its use in cancer chemotherapy has been studied for years [Breslow, D. S. *Pure and Applied Chem.* 46, 103 (1976)]. Polyacrylic, polymethacrylic and a variety of other aliphatic backbone water soluble polymers also have been shown to have a broad spectrum of biological activities [W. Regelson et al., *Nature* 186, 778 (1960)]. Unfortunately, the extreme toxicity of these polymers has prevented their clinical use. Also, these polymers have a high molecular weight and are unable to pass through the renal membranes.

Attempts have been made to circumvent the toxicity and excretion problems by synthesis of low molecular weight (1,000 to 10,000) aliphatic polymers [R. M. Ottenbrite in "Biological Activities of Polymers", *Amer. Chem. Soc. Symp.* Ser. No. 182, pp. 205–220, eds. C. E. Carraher and C. G. Gebelein (1982)]. It has been found that such polymers are less toxic but have much reduced antiviral activity. These low molecular weight aliphatic polymers may be classed as "random coil" polymers. Such polymers have an unpredictable configuration because of the flexibility of the backbone linking groups. The configuration of random coil polymers in solution may be generally described as globular. Although the mechanism of action of such water-soluble polymers is unknown, one postulate is that the polymer binds to the viral membrane, e.g. the virus causing encephelomyocarditis, through an ionic attraction, thus rendering the virus unable to infect host cells.

An additional synthetic polymer approach is to place ionic groups on the backbone of a polymer which exhibits a more defined geometry. There are numerous examples of non-ionic, synthetic polymers which exhibit a more linear geometry in non-aqueous solution than do the aliphatic polymers described above [*J. Macromol. Sci-Reviews in Macromol. Chem. Phys.* C26(4), 551 (1986)]. The factors involved which cause this non-random coil structure are complex and poorly understood. In general, such polymers have either a very limited number of rotatable bonds which are not parallel to the polymer axis, or there is hydrogen bonding or dipolar interactions which favor linear structures. These polymers are referred to as having a "rigid backbone". A polyamide derived from terephthalic acid and p-diaminobenzene (known commercially as Kevlar™ supplied by DuPont) is a well-known example of such polymers.

Synthetic, water-soluble, rigid polymers are much less common, but a few high molecular weight examples are known (e.g. see U.S. Pat. Nos. 4,824,916 and 4,895,660). The non-random coil structure of this class of polymer results in high solution viscosities for a given molecular weight and concentration.

Certain anionic oligomers which inhibit viral replication without the side effects shown by heparin and known polymers have now been found. The oligomers have an ordered anion spacing, have a rigid backbone and are water-soluble. The oligomers, as polydispersed mixtures, have been described in our copending U.S. patent application Ser. No. 710,370, filed Jun. 10, 1991, and PCT patent application Ser. No. PCT/US91/04804, filed Jul. 8, 1991, the disclosures of which are hereby incorporated by reference. Although various anionic oligomers are disclosed in these applications, all the anionic oligomers were mixtures of molecular weights.

Clearly, it would be desirable to find a treatment and cure for AIDS, ARC and HSV which would display minimal or no side effects and constitute a clear improvement over the polymers previously employed as a pharmaceutical. Also such oligomers should preferably have a narrow molecular weight ranger low toxicity and be easily characterized.

BRIEF DESCRIPTION OF THE DRAWINGS

FIG. 1 shows a crude polydisperse sulfonated polyurea of Formula I with a broad polydispersity as a starting material.

FIG. 2 shows the reduction in dispersity after Step 1, as defined on page 11, from the crude polydispersed sulfonated polyurea from FIG. 1 to a narrow polydispersity sulfonated polyurea, as one of several fractions.

FIG. 3 shows the combination of fraction 7 through 17 from the gel filtration chromatography of the crude polydispersed oligomer of FIG. 1, as a recombination of fractions from FIG. 2.

FIG. 4 shows monodispersed sulfonated polyurea oligomer fractionated from crude polydispersed oligomer of FIG. 1 using reverse phase liquid chromatography.

In FIGS. 5–9 the vertical axis is relative absorbance and the horizonal axis is time in minutes.

FIG. 5 shows various HPLC profiles of a polyurea of Formula I.

FIG. 6 shows an HPLC profile of a narrow polydispersed polyurea of Formula I using an aqueous triethylamine acetate ($Et_3NHOAc$) as eluent.

FIG. 7 shows an HPLC profile of a narrow polydispersed polyurea of Formula I using an aqueous tetrabutyl ammonium phosphate [$n-Bu_4N)PO_4$] as eluent.

FIG. 8 shows an HPLC profile of a monodispersed polyurea fractions of Formula I from FIG. 6 using an aqueous tetrabutyl ammonium phosphate [$n-Bu_4N)PO_4$] as eluent.

FIG. 9 shows a histogram of $IC_{50}$ antiviral concentrations of various oligomer fractions of a polydispersed and monodispersed polyureas of Formula I.

SUMMARY OF THE INVENTION

Figure 1:
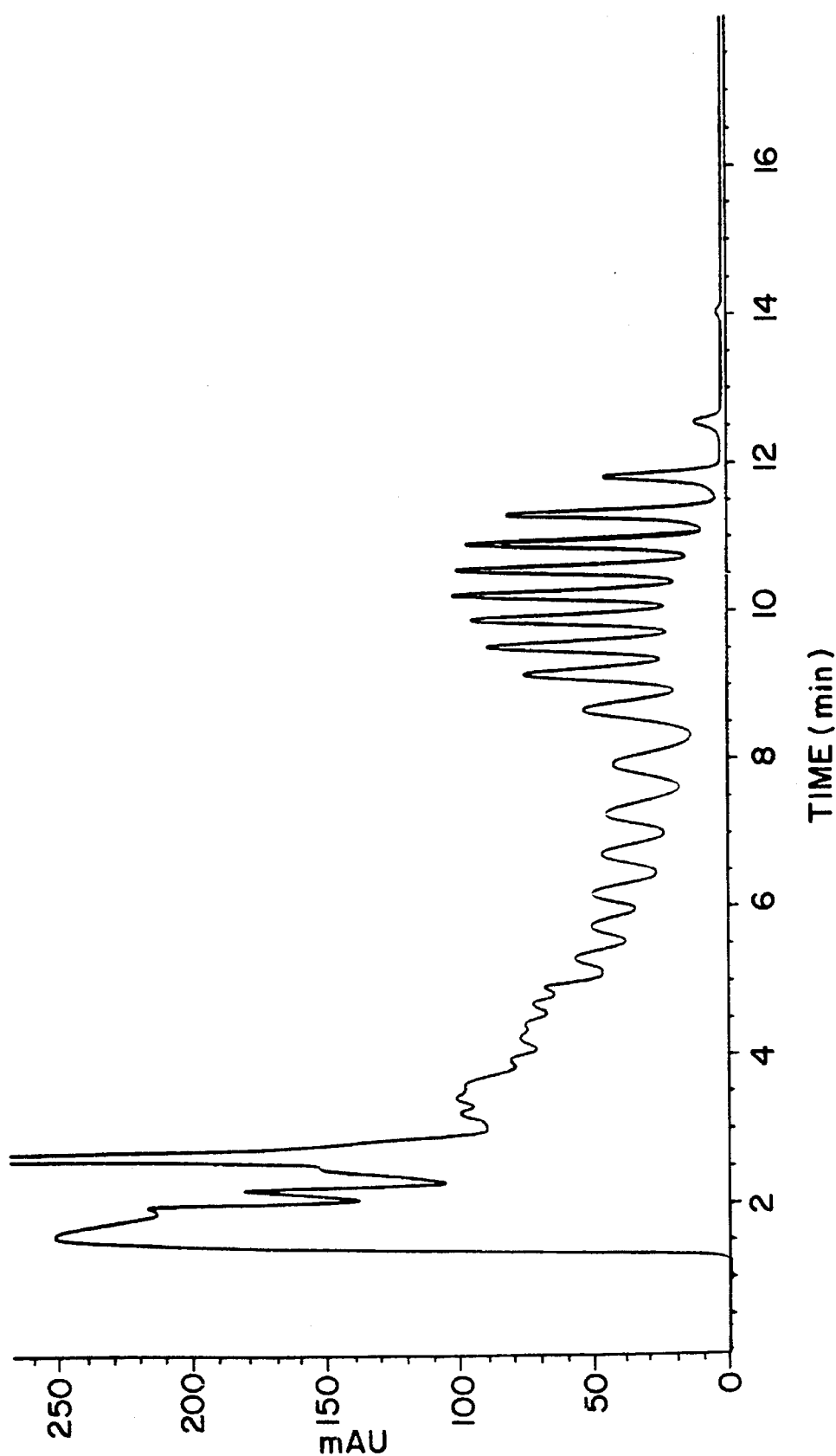
In FIGS. 1–4, the vertical axis is UV absorbance and the horizonal axis is time in minutes.

The present invention concerns narrow poly- and monodispersed, water-soluble oligomers comprising recurring units from 3 to 50 that are coupled by carbonyl linking moities, said oligomers having anionic groups and predominantly linear geometry such that regular spacing between anionic groups exists in an aqueous medium. Preferred oligomers of this invention are represented by any one of Formulae I–IV below.

A process of the present invention prepares the narrow poly- and mono-dispersed anionic oligomers of the invention, especially as represented by Formulae I–IV below, by the steps of:

1) restricting the crude polydispersed anionic oligomer mixture to a narrow polydispersed anionic oligomer mixture; and/or
2) isolating the monodispersed anionic oligomer; and
3) optionally converting the narrow poly- or mono-dispersed anionic oligomer salt from Step 1 or 2 to a desired pharmaceutically-acceptable salt, especially a sodium or potassium salt.

In the above process, the following combination of steps are intended: Step 1 or 2 is done alone; Step 1 or 2 is followed by step 3; or all three steps are done.

The narrow poly- and mono-dispersed oligomers are useful as anti-human immunodeficiency virus activity and anti-herpes simplex virus agents and these oligomers are thus useful in the treatment of AIDS, ARC and HSV. The present invention includes the narrow poly- and monodispersed oligomers, their formulation and use as agents for the treatment of AIDS, ARC and HSV and the process to prepare them.

DETAILED DESCRIPTION OF THE INVENTION

The narrow poly- and mono-dispersed, anionic oligomers of the present invention are water-soluble oligomers comprising recurring units from 3 to 50 that are coupled by carbonyl linking moities, said oligomers having anionic groups and predominantly linear geometry such that regular spacing between anionic groups exists in an aqueous medium. Preferably these oligomers are represented by any one of the following formulae:

A) a polyurea of the formula:

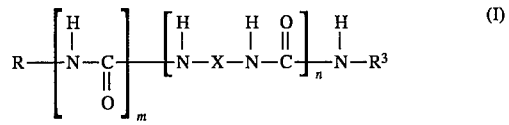

wherein:

R represents a hydrogen atom, a $C_1$–$C_4$ alkyl group, a phenyl group, or a phenyl group substituted with from 1 to 2 $R^1$ moities and up to 3 substituents independently selected from a fluoro, chloro or bromo atom or $C_1$–$C_{20}$ alkyl group;

$R^1$ represents —$SO_3R_2$, —$CO_2R^2$, —$PO_3(R^2)_2$, or —$OPO_3R^2$;

$R^2$ represents a hydrogen atom or a pharmaceutically-acceptable cation;

m is an integer 0 or 1, with the proviso that when m is 0, R is a hydrogen atom;

X represents

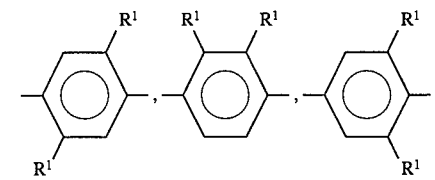

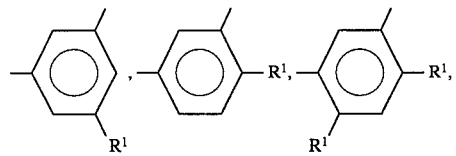

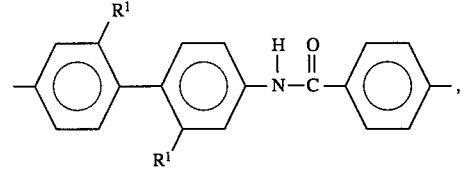

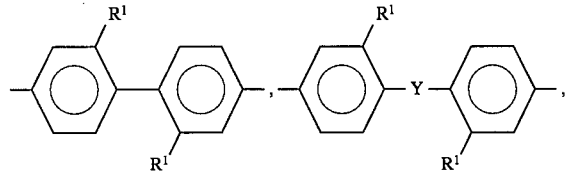

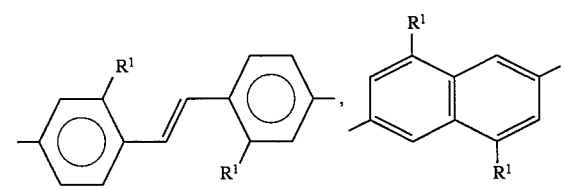

or

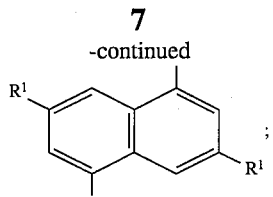

Y represents —$CO_2$—, —C≡C—, —N=N—,

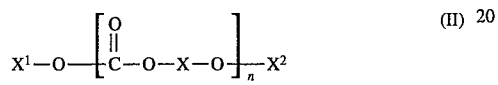

n is an integer from 3 to 50; and $R^3$ represents —R or —X—$NH_2$, where R and X are defined as before;

B) a polycarbonate of the formula:

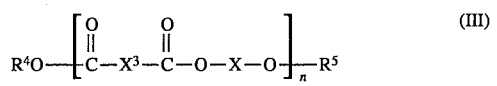     (II)

wherein;

X and n are defined as in Formula I above;

$X^1$ represents a HO—X— group, where X is defined as for Formula I above, or a $C_1$–$C_4$ alkyl group, a phenyl group, or a phenyl group substituted with from 1 to 2 $R^1$ moieties and up to 3 substituents independently selected from a fluoro, chloro or bromo atom or $C_1$–$C_{20}$ alkyl group; and $X^2$ represents a hydrogen atom or —$CO_2X^1$, where $X^1$ is defined as above;

C) a polyester of the formula

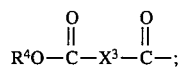     (III)

wherein:

X and n are defined as in Formula I above;

$R^4$ represents —$R^2$, as defined in Formula I, or —$X^1$, as defined in Formula II above;

$R^5$ represents $$R^4O-\overset{O}{\underset{\|}{C}}-X^3-\overset{O}{\underset{\|}{C}}-;$$

where $R^4$ is defined as in Formula III above, or —$R^2$, where $R^2$ is defined as in Formula I above;

$X^3$ represents

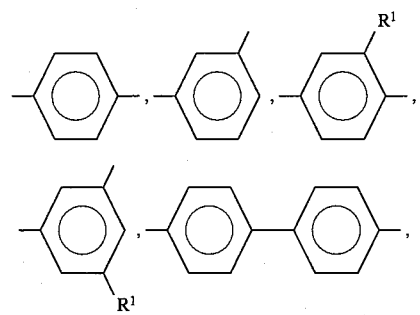

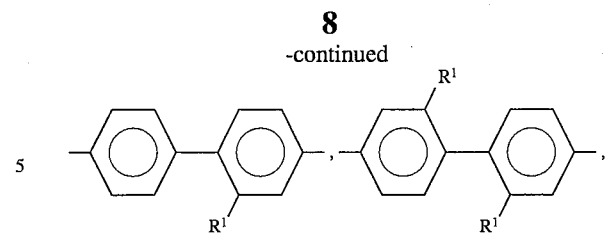

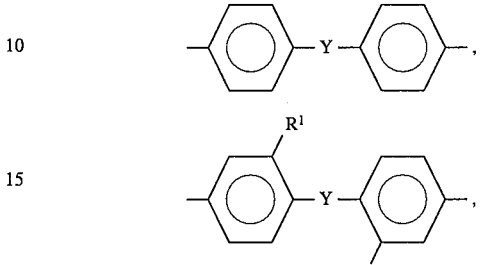

wherein $R^1$ and Y are defined as in Formula I above; or

D) a polyamide of the formula:

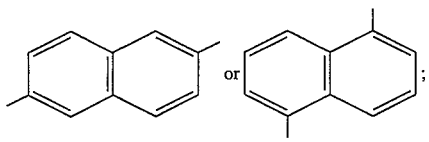     (IV)

wherein:

X and n are defined as in Formula I above;

$X^3$ is defined as in Formula III above;

$R^6$ represents $H_2N$—X—NH—, $R^2O$—, RNH— or R—C(O)—NH—X—NH—, where R, $R^2$ and X are defined as in Formula I;

$R^7$ represents a hydrogen atom,

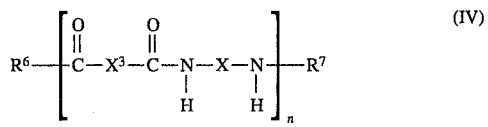

where R and $R^2$ are defined as in Formula I above; and $X^3$ is defined as in Formula III above.

Definitions

The terms used in the present application are defined as follows:

The term "$C_1$–$C_{20}$ alkyl", encompassing "$C_1$–$C_4$ alkyl", includes both branched and straight chained groups, such as, for example, methyl, ethyl, isopropyl, t-butyl, n-decyl, n-dodecyl and the like.

The term "pharmaceutically-acceptable cation" means a cation acceptable for pharmaceutical use. Those cations that are not substantially toxic at the dosage administered to achieve the desired effect and do not independently possess significant pharmacological activity are included within the term "pharmaceutically-acceptable cation". Illustratively, these salts include those of alkali metals, such as sodium and potassium; alkaline earth metals, such as calcium and magnesium; ammonium; light metals of Group IIIA including aluminum; and organic cations derived from primary, secondary and tertiary amines, ammonium or alkyl ammonium, especially tertiary ammonium salts. Examples include trialkylamines, including triethylamine, procaine, dibenzylamine, N,N'-dibenzylethylenediamine, dihydroabietylamine, N-($C_1$–$C_4$)alkylpiperidine, and any other suitable amine. Sodium and potassium salts are preferred. The term "pharmaceutically-acceptable" means suitable for administration to warmblooded animals, especially human beings, and includes being nontoxic, e.g. suitable for pharmaceutical use and is not poisonous to the warm-blooded animal. The pharmaceutically-acceptable cations of the oligomers of the present invention are prepared by conventional ion exchange processes or by treating the $R^1$ acid with an appropriate base. Particularly, the triethyl ammonium salts that are prepared as a part of the process (Step 2) are converted to more preferred pharmaceutically acceptable salts such as the sodium salt.

The oligomers of the present invention are narrow poly- and mono-dispersed, low molecular weight water-soluble polymers. Additionally, the oligomers have ordered anion spacing. By "ordered anion spacing" or "regular spacing between anionic groups" is meant that the anionic groups ($R^1$) are present in the backbone of the polymer at intervals determined by the starting material reagent used and the occurrence of the anionic groups is controlled in a predictable manner. While not wishing to be bound by any theory, the anionic groups of the oligomers are believed to be the portion that binds to the HIV, HSV and/or cell membrane and thereby interrupts the ability of the virus to replicate.

The terms "predominantly linear geometry" in an aqueous medium refers to the solution configuration of the oligomer. A method well known in the art for characterization of the solution configuration of polymer molecules is based on the following formula, referred to as the Mark-Houwink equation ["Introduction to Physical Polymer Science", ed. L. H. Sperling, pub. John Wiley & SONS (1985), pp. 81–83], $$[\eta]=KM^\alpha$$

wherein $\eta$ is intrinsic viscosity; M is weight average molecular weight; K is a constant related to chain bond dimension; and $\alpha$ is a constant determined by polymer configuration. The $\alpha$ constant for a random coil polymer is $0.5<\alpha<0.8$; and for a linear polymer is $0.8<=\alpha 1.8$. This formula relates the solution viscosity "$\eta$" to the molecular weight "M". For this invention linear polymers are defined as having "$\alpha$" values greater than or equal to 0.8. For a rigid rod polymer the theoretical upper limit is 1.8. For a given molecular weight, a higher solution viscosity will be obtained from polymers with a linear configuration relative to those polymers which exist as a random coil. An additional consideration is that the "$\alpha$" value is a function of the solvent used. The "$\alpha$" for a given water soluble polymer may be different at different salt concentrations. For this invention, the salt concentration is set at the levels present in serum (approximately 80 g/L NaCl, 4 g/L KCl).

Figure 2:
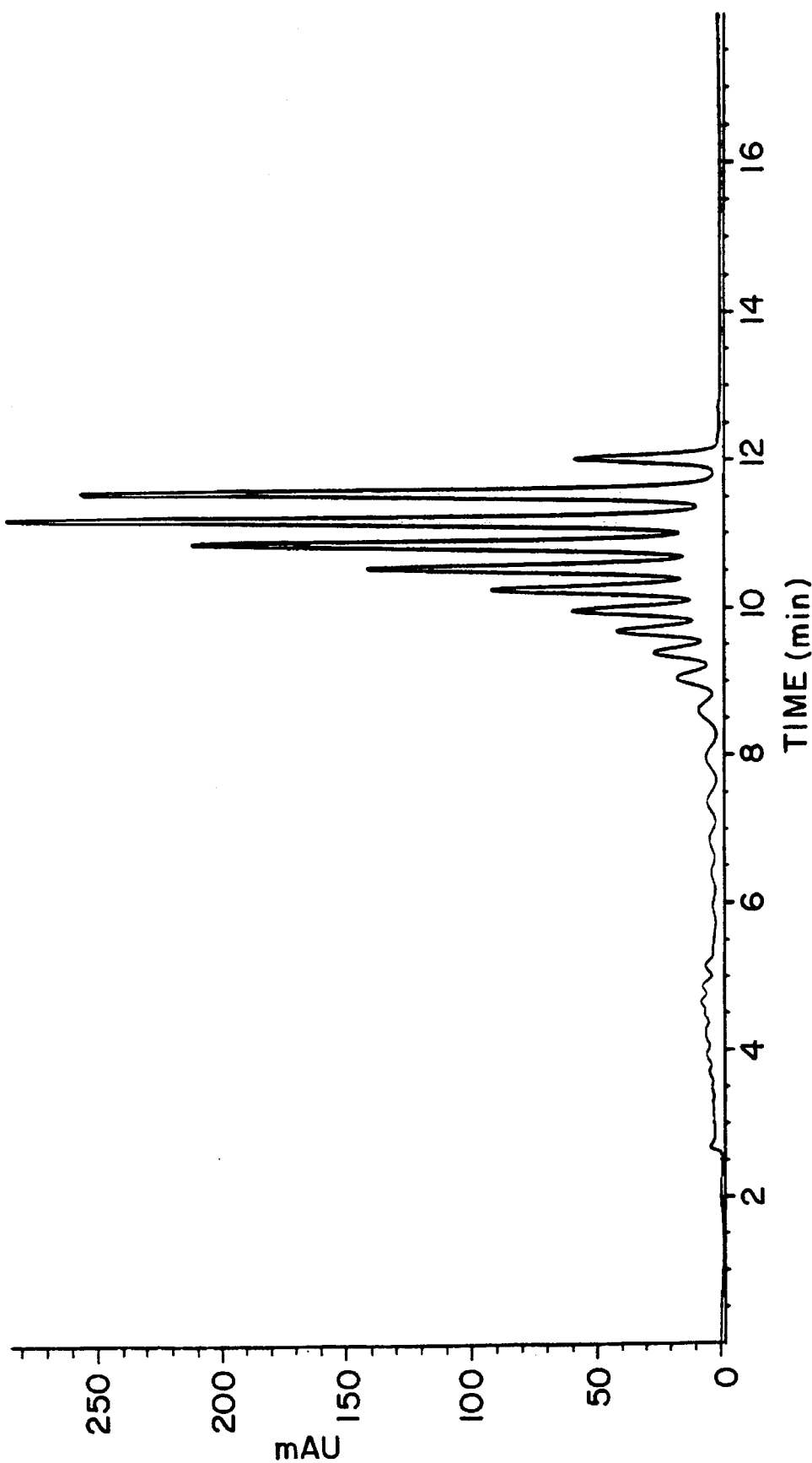

The terms "monodispersed" and "polydispersed" oligomers (and similar terms) refers to the distribution of oligomers in the sample. The polydispersity in a sample is measured by the ratio of the weight average molecular weight, $M_w$, to the number average molecular weight, $M_n$. (See G. Odian, "Principles of Polymerization", 2d ed pp 20–25, John Wiley & Sons, 1981.) For the purposes of this invention, "crude polydispersed" oligomer samples are $M_w/M_n=>1.3$ (see FIG. 1). For the purposes of this invention, an oligomer is a "narrow polydispersed" oligomer when $M_w/M_n=1.0$ to 1.3 (see FIG. 2); preferably from 1.0 to 1.2; and more preferably from 1.0 to 1.15. The narrow polydispersed oligomer has been prepared from the crude polydispersed oligomer mixture. For the purposes of this invention, an oligomer is a "monodispersed" oligomer when $M_w/M_n=1.0$ to 1.1 (see FIG. 4), which is a narrower range within the narrow polydispersed range. The term "narrow molecular weight range" refers to the decrease of the polydispersity ratio by some amount compared to the prior sample.

The term "rigid backbone" means that the recurring unit, also referred to as a repeat unit, is composed predominantly of groups which limit rotation away from the chain axis. For example, p-phenylene and amide groups —(C(O)—NR—) do not bend easily away from the chain axis. A limited number of bent groups are tolerable in the chain axis, such as m-phenylene and urea. The oligomers of the present invention preferably have such a rigid backbone.

The purity of each monodispersed fraction of any desired n fraction is at least 75%, preferably from about 85 to about 100%. Purity is defined as the area ratio of the desired oligomer relative to the area of all peaks observed on an analysis by HPLC.

As used herein, the term "oligomer" encompasses all the possible values for n, e.g., 3 through 50. The oligomers are preferably linear with n equal to an integer from 3 to 50, preferably from 3 to 15, more preferably from 5 to 10, most preferably 6 to 9. Of course, the molecular weight is directly related to the n value of the resulting oligomer. It is essential that these oligomers are of sufficiently low molecular weight in order to pass through the renal excretory membrane, but able to inhibit the HIV virus.

For the purpose of the present invention, the oligomers described herein and physiologically-acceptable salts thereof are considered equivalent. Physiologically-acceptable salts refer to the salts of those bases which will form a salt with at least one acid group of the $R^1$ group and which will not cause significant adverse physiological effects when administered as described herein. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary and tertiary amines and the like. Particularly preferred bases are the alkali metal hydroxides, carbonates, and bicarbonates. Physiologically-acceptable salts may be prepared by conventional ion exchange processes or by treating the $R^1$ acid with an appropriate base. Examples of additional salts have been described herein.

The formulations of the present invention are in the solid or liquid form. These formulations may be in kit form such that the components are mixed at the appropriate time prior to use. Whether premixed or as a kit, the formulations usually require a pharmaceutically-acceptable carrier or adjuvant.

The oligomers of the present invention are soluble in water and in salt solutions, especially at physiological pH and in saline solutions. Thus the present oligomers are readily formulated into a suitable aqueous pharmaceutical dosage form. Also, after the present oligomer formulation is administered, the oligomer remains soluble in vivo.

Preferred terms for the previously described Formulae I to IV are as follows:

R and $R^3$ are a 4-methylphenyl group;

m is 1;

n is 3 to 15;

$R^4$ and $R^5$ are hydrogen;

$R^6$ is phenyl;

$R^7$ is benzoyl;

$X^1$ is a 4-methylphenyl group;

$X^2$ is —$CO_2$—(4-methylphenyl) group;

$X^3$ represents

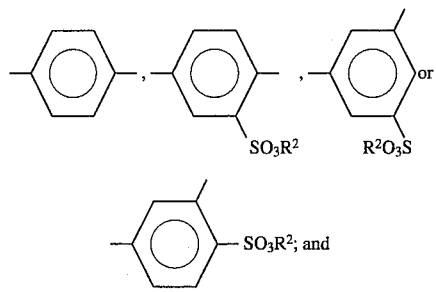

x represents

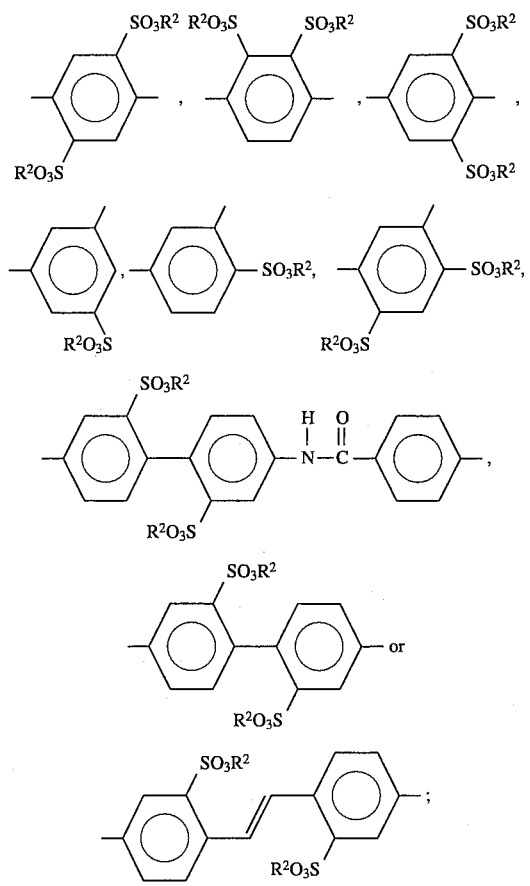

while especially preferred is

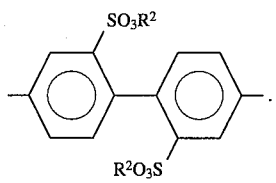

Particularly preferred are the polyureas of Formula I where R and $R^3$ are a 4-methylphenyl group; m is 1; n is 3 to 15; X represents

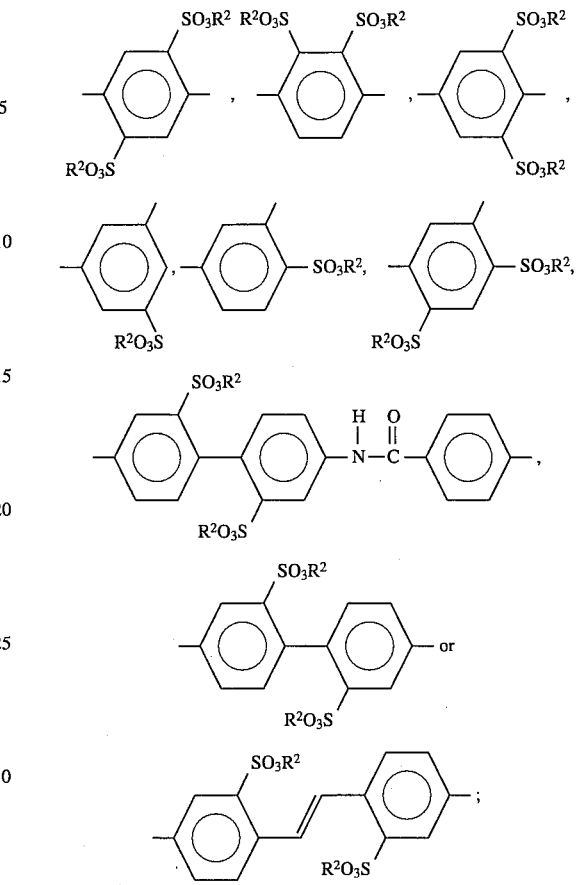

and $R^2$ is defined as before. Specific examples of such polyureas are:

StDS/P/T=poly[imino(3-sulfo-1,4-phenylene)- 1,2-ethenediyl-(2-sulfo-1,4-phenylene)iminocarbonyl], alpha-{[(4-methylphenyl)aminocarbonyl}-omega-[(4-methylphenyl)-amino- and is represented by Formula I above when R and $R^3$ is 4-methylphenyl, $R^2$ is hydrogen, X is

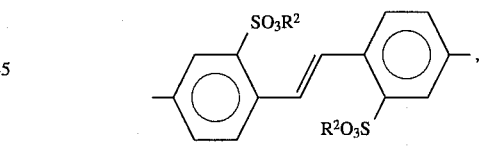

PDS/P/T=poly[imino(2,5-disulfo-1,4-phenylene)iminocarbonyl], alpha-{[(4methylphenyl)amino] carbonyl}-omega-[(4methylphenyl)amino] - and is represented by Formula I above when R and $R^3$ is 4-methylphenyl, $R^2$ is hydrogen, X is

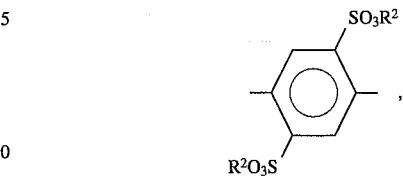

BPDS/P/T=poly{imino[2,2'-disulfo(1,1'-biphenyl)- 4,4'-diyl]iminocarbonyl}, alpha-{[(4-methylphenyl)amino] -carbonyl}-omega-[(4-methylphenyl)amino] - and is represented by Formula I above when R is 4-methylphenyl, $R^2$ is hydrogen, X is

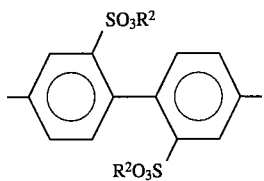

and especially when n is 5, 6, 7, 8, 9 or 10.

Particularly preferred are the polycarbonates of Formula II wherein $X^1$ is 4-methylphenyl; $X^2$ is —$CO_2$—( 4-methylphenyl); n is 3 to 15; and X is

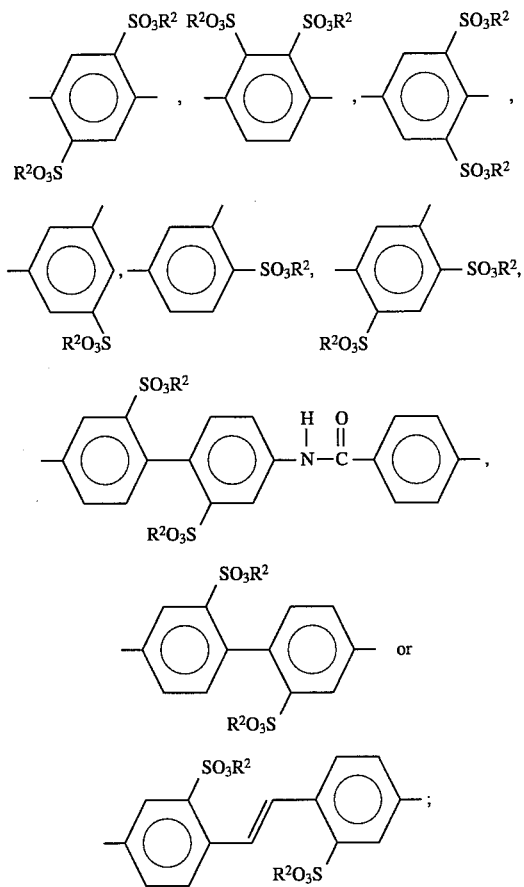

Specific examples of such polycarbonates are:
HBDS/P/C=poly[oxy(2,5-disulfo-1,4phenylene)oxycarbonyl], alpha-[(4-methylphenoxy)-carbonyl] -omega-(4-methylphenoxy)- and is represented by Formula II above when $X^1$ is 4-methylphenyl, $R^2$ is hydrogen, X is

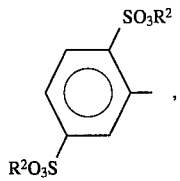

$X^2$ is

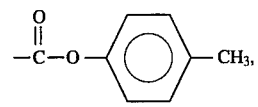

and n is an integer from 3 to 15.

HBPDS/P/C=poly{oxy[2,2'-disulfo(1,1' -biphenyl)-4,4'-diyl]oxycarbonyl}, alpha-[(4-methylphenoxy)carbonyl] -omega-(4-methylphenoxy)- and is represented by Formula II above when $X^1$ is 4-methylphenyl, $R^2$ is hydrogen, X is

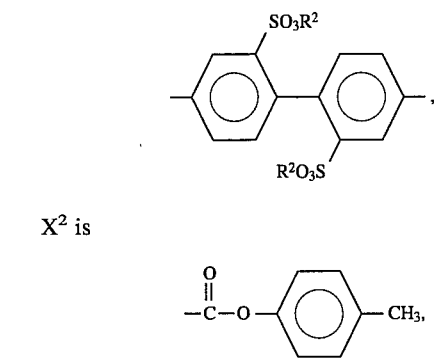

$X^2$ is

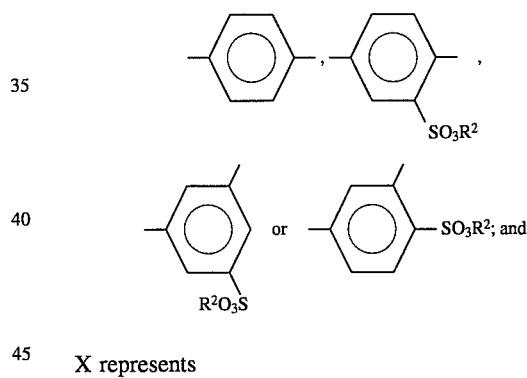

and n is an integer from 3 to 15.

Particularly preferred are the polyesters of Formula III wherein $R^4$ and $R^5$ are hydrogen; n is 3 to 15; and $X^3$ represents

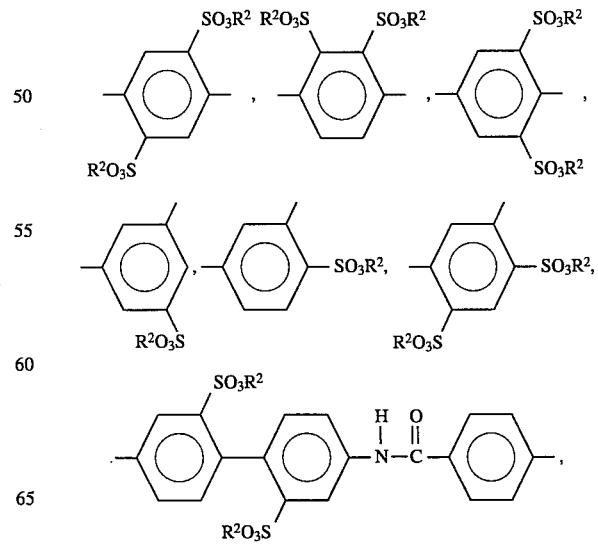

X represents and X represents

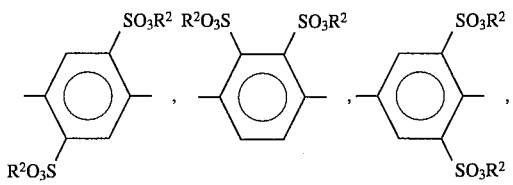

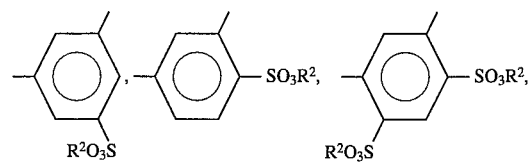

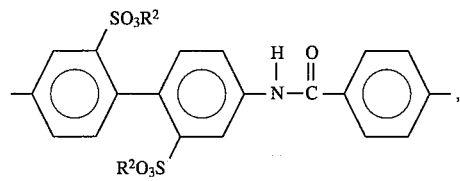

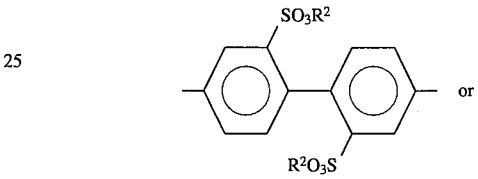

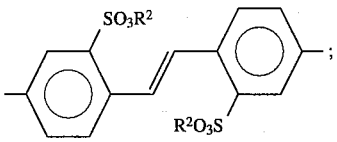

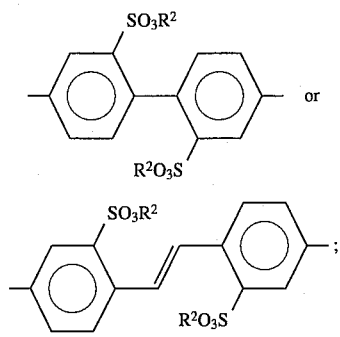 or

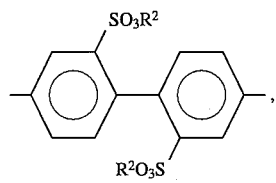 ;

Specific examples of such polyesters are:

HBPDS/TPC=poly{oxy[2,2'-disulfo(1,1'-biphenyl)-4,4'-diyl]oxycarbonyl-1,4-phenylenecarbonyl}- and is represented by Formula III above when $R^4$ and $R^5$ are hydrogen, $X^3$ is p-phenylene, X is

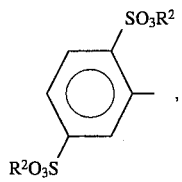, and n is an integer from 3 to 15.

HBDS/TPC=poly[oxy(2,5-disulfo-1,4-phenylene)-oxycarbonyl-1,4-phenylenecarbonyl]- and is represented by Formula III above when $R^4$ and $R^5$ are hydrogen, $X^3$ is p-phenylene, X is

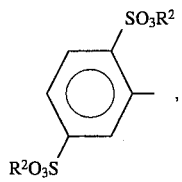, and n is an integer from 3 to 15.

Particularly preferred are the polyamides of Formula IV wherein $R^6$ is phenyl; $R^7$ is methyl benzoyl; n is 3 to 15; and $X^3$ represents

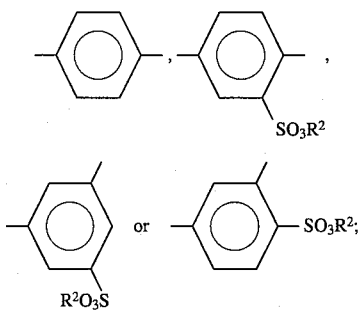

Specific examples of such polyamides are:

BPDS/TPC/MBC=poly{imino[2,2'-disulfo(1,1'-biphenyl)- 4,4'-diyl]iminocarbonyl-1,4-phenylenecarbonyl}, alpha-{[(4-methylphenyl)amino]carbonyl}-omega-[(4-methylphenyl)amino] - and is represented by Formula IV above when $R^6$ is R—C(O)—NH—X—NH—, R is 4-methylphenyl, $R^2$ is hydrogen, $R^7$ is 4-methylbenzoyl, $X^3$ is p-phenylene, X is

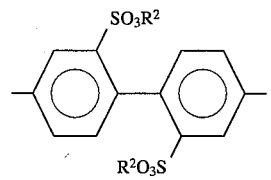

and n is an integer from 3 to 15.

The present invention concerns a process for the preparation of narrow poly- and mono-dispersed anionic oligomers that have a narrow molecular weight range which enables these oligomers to be used as pharmaceutical agents, particularly in humans, for the treatment of AIDS or ARC. The resulting advantages of having a narrow molecular weight range for these oligomers are greater activity than the corresponding mixtures and better characterization of the oligomers.

The present invention is directed to a process for the isolation of the above oligomers into their individual components, e.g. a narrow molecular weight range, and to the isolated oligomer product so prepared.

In the process to prepare the narrow poly- and monodispersed anionic oligomers of the present invention, the various steps may be performed in the following manner.

Step 1—restricting the crude polydispersed anionic oligomer mixture to a narrow polydispersed anionic oligomer mixture—may be accomplished by gel filtration, selective precipitation, membrane permeation, or reverse phase chromatography; and/or Step 2—isolating the monodispersed anionic oligomer—may be accomplished by gel electrophoresis or reverse phase chromatography. The monodispersed purity of each desired n fraction is at least 75%, preferably from about 85 to about 100%; and Step 3—optionally converting the narrow poly- or monodispersed anionic oligomer salt from Step 1 or 2 to a desired pharmaceutically-acceptable salt, especially the sodium or potassium salt—may be accomplished by either ion exchange, particularly when the tetrabutyl ammonium salt has been formed, or by the addition of a salt of a weak, volatile acid.

In the process of the present invention, the methods employed are those customary and known in the art. As these techniques are known, some examples of a description of these methods can be found as follows:

Gel filtration—"Protein Purification", ed. Charles R. Cantor, Springer-Verlag, 1987, in the chapter by Robert K. Scopes, "Separation in Solution", pp 186– 198.

Selective precipitation—"Polymer Fractionation", ed. Manfred J. R. Cantow, Academic Press, 1967, in the chapter by Akira Kotera, "Fractional Precipitation", pp. 43–65.

Membrane permeation—"Polymer Fractionation", ed. Manfred J. R. Cantow, Academic Press, 1967, pp. 462.

Reverse phase chromatography—*J. Chrom. Library*, 41A, "High-Performance Liquid Chromatography of Biopolymers and Biooligomers", ed. O. Mikes, Elsevier, 1988, pp. A127–A208, A303–A399.

Gel electrophoresis—"Protein Purification", ed. Charles R. Cantor, Springer-Verlag, 1987, in the chapter by Robert K. Scopes, "Separation in Solution", pp 199–215.

Ion exchange—"Dowex::Ion Exchange", The Dow Chemical Company, The Lakeside Press, 1958, pp. 39–66.

Addition of a salt of a weak, volatile acid oligomers in solution as ammonium salts of volatile amines can be converted to more preferred pharmaceutically-acceptable salts, such as the sodium or potassium salts, by treating the solution with an alkali metal salt of a weak volatile acid. Upon concentrating the solution by evaporation or lypholization, the amine and weak acid are removed and the oligomers are isolated as their alkali metal salts. Suitable examples of ammonium salts which may be converted in the step are salts of ammonia, monoethylamine, triethylamine, trimethylamine or dimethylamine (herein to as "ammonium salts"). Examples of alkali metal salts are sodium or potassium hydroxide, bicarbonate, acetate, formate or propionate.

Preparation of the Crude Polydispersed Anionic Oligomer Starting Materials.

The crude polydispersed anionic oligomers used as starting materials in the process of the present invention to prepare the narrow poly- and mono-dispersed anionic oligomers of the present invention are prepared by the process described in our copending U.S. patent application Ser. No. 710,370, filed Jun. 10, 1991, the disclosure of which is hereby incorporated by reference. The process to prepare these polydispersed oligomers uses a modification of the procedure of Kershner (U.S. Pat. No. 4,895,660, the disclosure of which is hereby incorporated by reference, and described further below) by replacing a portion of one of the difunctional monomers with a mono-functional end-capping agent and running the reaction in the absence of a surfactant. The number average molecular weight ($M_n$) is governed by the stoichiometry of the reactants.

The polydispersed anionic oligomers are prepared by the various reactions described below.

Polydispersed Polyureas and Polyamides (of Formulae I and III above.)

The preferred process for the polydispersed polyureas and polyamides of Formulae I and III above is described in the art (Kershner U.S. Pat. No. 4,824,916) and is further explained as follows. The various reactants and conditions are also described.

Diamines: A wide variety of aromatic diamines are included. The range of possible substituents is similarly broad, and includes hydroxyl, alkenyl, lower alkyl moieties, carboxylate, sulfonate, and halogens. The substituents are not necessarily anionic at neutral pH in water.

Difunctional Electrophiles: Phosgene (carbonyl dichloride), carbonyl dibromide, $Cl_3COCOCl$, carbonyl diimidazole, $Cl_3COCO_2CCl_3$, diacid halides of aromatic dibasic acids such as terphthalic, isophthalic, 2,6-naphalenedioic acids.

Acid Acceptors: Several bases have been employed, such as sodium carbonate, sodium hydroxide, and tributylamine.

Miscellaneous additives: Various surfactants may be added. Suitable surfactants may be non-ionic, such as sorbitan monolaurate, sorbitan monostearate, ethylene glycol distearate, polyethylene oxy/polypropylene oxy polymer. Such surfactants can be difficult to remove from the product, and therefore the use of surfactants is not preferred.

Solvents: Single solvent processes employ polar aprotic solvents such as N,N-dimethylacetamide and N,N-dimethylformamide. Also applicable are a combination of water and a second solvent, such as toluene, carbon tetrachloride, benzene, acetone, ethylene dichloride, and the like. Typical ratios of organic to aqueous solvents are about 0.5 to about 2.

In the processes described in the art, the diacid halide is added to a stirred solution or suspension of the other starting materials. In some instances the base is added during the diacid halide addition. The temperature is maintained between 0° and 50° C., preferably 20° to 30° C. A reactant ratio (molar ratio of diamine to diacid halide) from about 0.9 to 1.2 may be used, with essentially equimolar amounts preferred.

The reaction is stirred at a rate sufficient to achieve mixing of the reactants. The reaction rate is dependent in part on the interfacial area between the phases, and therefore vigorous stirring is preferable. A commercial blender may be employed for this purpose.

The process used to prepared the polydispersed polyureas is a modification of the process described above.

Diamines: The diamines of the present invention are primarily aromatic, with the formulae described in previous sections. Such diamines are substituted with at least one group which is charged at neutral pH, preferable sulfonate. Monovalent aliphatic substituents are allowable. A small set of aliphatic linking groups which tie aromatic radicals together may be used such as trans-substituted ethylene and acetylene. Preferred diamines are those in which the carbon-nitrogen bonds are forced to be parallel, such as 2,5-diamino-1,4-benzenedisulfonic acid (PDS), 4,4'-diamino-(1,1'-biphenyl)-2,2'disulfonic acid (BPDS), trans-2,2'-(1,2-ethenediyl)bis(5-aminobenzenesulfonic acid) (StDS), and 2,5-diaminobenzensulfonic acid.

Difunctional electrophiles: For the preparation of polyureas phosgene (carbonyl dichloride) and carbonyl dibromide, and other urea precursors such as carbonyl diimidazole, hexachloroacetone, $Cl_3COCO_2CCl_3$, $CCl_3COCl$, and $Cl_3COCOCl$ may be used.

Acid Acceptors: A variety of inorganic bases may be used, such as alkali metal or divalent metal hydroxides carbonates, bicarbonates, phosphates. Acid acceptors with buffering capacity are preferred when all of the base is added prior to the addition of the difunctional electrophile. Organic bases such as trialkyl amines may be used, but are not preferred.

Monofunctional end capping agent: A variety of such molecular weight limiting agents may be used. Such agents may be aliphatic or aromatic compounds which react with the diamines or the difunctional electrophiles. Examples of suitable monofunctional agents are amines such as aniline, methylaniline, methylamine, ethylamine, butylamine, diethylamine, ammonia, N-methylaniline, phenol and cresol. Examples of monofunctional amine reactive agents are benzoyl chloride, methyl benzoyl chloride, acetyl chloride, and phenyl chloroformate. These end-capping agents may also contain charged substituents, for example potassium 2-sulfophenol or potassium 4-sulfoaniline.

Miscellaneous additives: The addition of surfactants is not necessary or preferred, and can complicate the isolation process.

Solvents: A single solvent, water, is preferred when the difunctional electrophile is a liquid at the reaction temperature. An example of such a difunctional electrophile is phosgene. When solid, water insoluble reactants are used, a small amount of a water immiscible cosolvent is desirable. Example of such water immiscible cosolvents are chloroform, carbon tetrachloride, toluene, and methylene chloride. Typical ratios of organic to aqueous solvents are 0 to 1, with 0 to 0.1 preferred.

The process is conducted at temperatures which allow the reaction to proceed, typically from about 0° to 100° C. Preferable temperatures are 0° to 25° C. When low boiling starting materials are used, for example phosgene (bp 6° C.), it is advantageous to operate at temperatures at or below the boiling point. The pressure is not important and typically ambient pressure is employed. The pH of the reaction must be carefully maintained for optimum process. At low pH (<6) the reaction is very slow, while at high pH (>10) the difunctional electrophile is unstable to attack by hydroxide or other base. Degradation of the polyurea can also occur at high pH. The pH is preferably maintained between 7 and 9.

When no end capping agent is used, molecular weight control can be achieved by careful adjustment of the stoichiometry of the reactants. Either the diamine or the difunctional electrophile may be used in excess, for example from 1 to 100% molar excess. This stoichiometry must account for any of the difunctional electrophile which is destroyed by hydrolysis prior to reaction with the diamine. For example, when phosgene is used at high pH, a large excess is required to compensate for the fast reaction with hydroxide which destroys it. Because the extent of this side reaction is difficult to control, a monofunctional end capping agent is preferably used to control the molecular weight. Although the techniques mentioned can be used to control the number average molecular weight, the products are mixtures of polymers with several molecular weights characterized by a distribution.

The order of addition of the reactants is not critical. However, the preferred order is to add the difunctional electrophile first. When acid acceptors which are not buffers are used, such as hydroxide, it is most preferable to add a portion at the beginning to achieve the desired pH, and then add the remainder concurrently with the difunctional electrophile.

Finally, it is desirable to conduct these polymerizations at high concentrations. This reduces the amount of solvent which must be removed to isolate the product. Also, in certain cases the product precipitates from the reaction solution near the end of the reaction, and may be isolated by simply decanting the solvent. Most of the inorganic salt which results from reaction of the acid acceptor is removed in this process. The concentration is not critical, and may be from 0.5 to 50 wt %, expressed as weight of diamine to weight of solvent. A preferred range is 1 to 10 wt %.

The crude polydispersed product may be isolated by precipitation of the reaction solution with a solvent which is water miscible but is a poor solvent for the product. Examples of such solvents are acetone, methanol, ethanol, isopropanol.

Polycarbonates and Polyesters (of Formulae II and IV above)

The process previously described for the polyureas and polyamides was used, with the following exceptions: Diphenols were used in place of the diamines: Suitable aromatic diphenols containing at least one substituent which is anionic at pH 7. These diphenols have identical structures to those of the diamines except that the amines are replaced with hydroxyl groups. It is possible to pretreat the diols with one or two moles of base to form the mono- or diphenoxides. Some specific examples are dipotassium 4,4'-dihydroxy(1, 1'-biphenyl)-2,2'-disulfonate (HBPDS) and dipotassium 2,5-dihydroxy-1,4-benzenedisulfonate (HBDS).

The process conditions are much more critical due to the instability of the products in aqueous solutions. Of particular importance is pH control. At pH levels below 7 the polymerization rate is very slow, while at high pH (>9) the carbonate or ester groups in the polymer undergo hydrolysis. A preferred pH range is 7 to 8, and it is desirable to use an automatic pH controller to maintain it. The useful range of temperatures under which the polymerization can be conducted is more narrow, 0° to 40° C., and preferably from 0° to 25° C.

After addition of the diacid chloride is complete, it is desirable to wait for a time, typically 15 to 120 minutes to insure that the conversion of starting materials is complete. Additional base may be added during this period, but the pH is never allowed to rise above the previously described limits. The crude polydispersed product is isolated as described above.

Methods of Using

The present narrow poly- and mono-dispersed anionic oligomers can be used to prevent syncytium formation in cells infected with HIV-I virus or other related viruses. Anti-HIV anionic oligomers can be used to treat AIDS and ARC and other diseases caused by the retrovirus HIV-I or other related viruses. The narrow poly- and mono-dispersed anionic oligomers of this invention can be used as a mixture where the polydispersity ratio is no greater than 1.3, or as a monodispersed oligomer, such as those of selected n values of a particular Formula I to IV, or mixtures of more than one Formula, e.g., Formula I with Formula II compounds, or as mixtures with other known agents for the present anti-viral utilities, such as 3'-azido-3'-deoxythymidine (AZT).

The amount of anti-HIV narrow poly- and mono-dispersed anionic oligomers which is needed to prevent syncytium formation in HIV infected cells can be any effective amount. Experimentally, it has been determined that anti-HIV anionic oligomers, when employed at a concentration of 10 μg/mL of aqueous formulation, resulted in complete inhibition of syncytium formation as well as reduced the presence of p24 antigen. The amount of anti-HIV anionic oligomers to be administered in order to treat AIDS, ARC or other diseases caused by HIV infection can vary widely according to the particular dosage unit employed, the period of treatment, the age and sex of the patient treated, the nature and extent of the disorder treated, and other factors well-known to those practicing the medical arts. Moreover anti-HIV anionic oligomers can be used in conjunction with other agents known to be useful in the treatment of retroviral diseases and agents known to be useful to treat the symptoms of and complications associated with diseases and conditions caused by retroviruses.

The anti-HIV effective amount of anti-HIV narrow poly- or mono-dispersed anionic oligomers to be administered according to the present invention will generally range from about 0.1 mg/kg to 500 mg/kg of body weight of the patient and can be administered one or more times per day. Anti-HIV anionic oligomers can be administered with a pharmaceutical carrier using conventional dosage unit forms either orally or parenterally.

The ability of the narrow poly- or mono-dispersed oligomers of this invention to act as anti-viral agents can be demonstrated by their ability to inhibit the growth and replication of HSV virus. Used herein the term "a method of treating a Herpes viral infection" refers a patient who as been infected with the Herpes virus, either type 1 or type 2, and administering to said patient a virally effective amount of a narrow poly- or mono-dispersed compound of Formulae I–IV. Futhermore, it is also understood that the term "viral infection" refers to any state or condition characterized by the virus residing in the cells or body of said patient.

Antiviral activity of the oligomers of the invention can be assessed by the plaque-reduction assay as previously described by Tyms et al., J. Antimicrobial Chemotherapy, 8, 65–72 (1981). Briefly, human embryonic fibroblast cells (MRC5) were cultured in 24-well tissue cultrue trays in the presence of Eagles' minimum essential medium (MEM) supplemented with 10% fetal calf serum. When cell monolayers were semi-confluent, they were inoculated with 30–50 plaque-forming units of HSV2 strain HG52 or HSV1 strain 17i [Davison & Wilkie, J. General Virology, 55, 315–331 (1981)]. At the end of an adsorption period of one hour at room temperature, infected monolayers were overlayed with MEM containing 2% fetal calf serum, 0.5% low-temperature gelling agarose and the antiviral compound at a range of concentrations. After 3 days incubation, cells were fixed in 10% formalin in saline and subsequently stained with 0.3% methylene blue. Dose-response lines were plotted from the mean number of plaques present versus the log of the concentration of the compound. The 50% effective dose (ED50) was computed after linear regression analysis.

The use of the narrow poly- or mono-dispersed anionic oligomers of this invention to treat HSV infections in humans is very important. The term "Herpes viral infection" means infections caused by either by the Herpes Type I Virus or the Herpes Type 2 Virus. The term "patient" used herein is taken to mean mammals such as primates, including humans, sheep, horses, cattle, pigs, dogs, cats, rats and mice.

The amount of the narrow poly- or mono-dispersed anionic oligomer of Formulae I–IV to be administered can vary widely according to the particular dosage unit employed, the period of treatment, the age and sex of the patient treated, the nature and extent of the disorder treated, and the particular anionic oligomer selected. Moreover the anionic oligomer can be used in conjunction with other agents known to be useful in the treatment of HSV and CMV infections and agents known to be useful to treat the symptoms of and complications associated with diseases and conditions caused by virus. The anti-Herpes virally and anticytomegalo-virally effective amount of anionic oligomer of Formula I to be administered will generally range from about 15 mg/kg to 500 mg/kg. A unit dosage may contain from 25 to 500 mg of anionic oligomer, and can be taken one or more times per day. The anionic oligomer can be administered with a pharmaceutical carrier using conventional dosage unit forms either orally, parenterally, or topically.

For oral administration, anti-HIV or anti HSV anionic oligomers can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, sorbitol, calcium phosphate, and cornstarch. In another embodiment the anionic oligomers of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene glycols, either with or without the addition of a pharmaceutically-acceptable surfactant, suspending agent, or emulsifying agent.

The anti-HIV or anti-HSV narrow poly- and mono-dispersed anionic oligomers of this invention may also be administered parenterally, that is, sub-cutaneously, intravenously, intramuscularly, or inter-peritoneally, as injectable dosages of the anionic oligomers in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of anti-HIV anionic oligomer in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate.

The narrow poly- and mono-dispersed anionic oligomers of this invention can also be used prophylactically, that is, to prevent transmission of virus from an infected individual to an uninfected target. Virus is spread proportionally via exchange of blood but may be transmitted via exchange of other bodily fluids as well. Thus the oligomers of this invention can be formulated with standard detergent products for use in cleaning, particularly in research and clinical laboratories and in hospitals where blood products of infected individuals are handled. Formulations containing the oligomers of the present invention can be used to clean medical/surgical equipment and utensils as well as the hands of and other skin areas of health care workers. The oligomers of this invention can also be applied, as a liquid or powder composition, to the surface of sexual prophylaxis such as condoms by either the user or manufacturer of the prophylaxis prior to sale. The oligomers of this invention can be formulated into a douche composition for use by females for use prior to subsequent sexual contact with an infected individual. The oligomers of this invention can also be formulated in lubricants and spermatacidal jellies and lotions. Finally, the oligomers of this invention can also be formulated as compositions to be added to hot tubs, whirlpool baths and swimming pools to inactivate potential virus activity.

The invention will be further clarified by a consideration of the following examples, which are intended to be purely exemplary of the present invention.

Definitions

The terms used in the present examples are defined as follows, unless stated otherwise, and for example represent an instance of suitable equipment or resins, but similar equipment or differing parameters or resins may be used:

Gel filtration column=Sephadex™ G-25 gel filtration column (3.0 cm×94 cm);

Peristaltic pump=Gilson Minipuls™ peristaltic pump;

UV detector=Isco model UA-5 ultraviolet detector;

HPLC=high performance liquid chromatography;

Membrane filter with 10,000 Dalton cutoff= Centricon-10 from Amicon;

Membrane filter with 3,000 Dalton cutoff= Centricon-3 from Amicon;

Liquid Chromatograph=Hewlett Packard™ 1090;

Diode Array Detector=280 nm or 320 nm or 550 UV with 4 nm or 100 bandwidth;

Reverse phase chromatography column I=Alltech Hyperprep™ 120 ODS;

Reverse phase chromatography column II= Alltech Absorbosphere™ HS high carbon loading C18;

Syringe cartridge column=Alltech Maxi-Clean™ SCX;

TCID50=tissue culture infectious dose, i.e. the amount of culture fluid effective to infect 50% of the cells (50% cytopathic effect) at 7 days post infection;

MTT=tetraazolium reduction reagent; 3-(4,5-dimethylthiazol- 2-yl)-2,5-diphenyltetrazolium bromide:

RPMI 1640=a standard cell culture media obtained from GIBCO;

MT4= a human T cell transformed cell line;

$IC_{50}$=inhibiting dose blocking 50% of virus growth; and pfu=plaque forming unit.

PREPARATION OF STARTING MATERIALS
FOR THIS PROCESS Example A: Bromo end-cap

A 4-neck flask was fitted with a syringe port, a thermometer well, mechanical stirring, a pH electrode, a dry ice condenser, and a phosgene gas inlet tube. The flask was charged with 8.00 g (23.23 mmol) of a 4,4'-biphenyl-2,2'-disulfonic acid. 0.961 g (5.162 mmol) of 2-bromo-4-methylaniline, and 250 mL of water. The flask was cooled to 12° C. and the stirred suspension treated with 11 mL of 5M sodium hydroxide until all the solids had dissolved and the pH had reached 11.5. To the mixture was added, over a 10 min period 4.5 g (45 mmol) of phosgene, along with additional 5M sodium hydroxide to maintain the pH between 8 and 9. After 3 hrs of stirring, 1.848 g (9.93 mmol) of additional 2-bromo-4-methylaniline was added together with 100 mL of water. Then 3.7 g (37 mmol) of additional phosgene was added, along with sufficient 5M sodium hydroxide to maintain the pH between 8 and 9. Stirring was continued overnight (about 16 hrs), and then the contents were precipitated into 1000 mL of acetone. The product was filtered and washed 3 times with 100 mL of acetone. The filter cake was then transfered to a crystallizing dish and dried in a vacuum oven overnight at 50° C. affording 11.249 g of crude off-white powder. The product formed has the formula

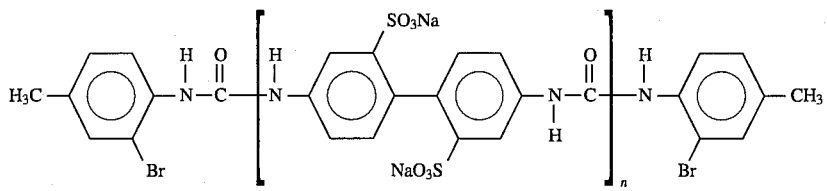

with a crude polydispersity of $M_w/M_n$ of about 1.4.

Example B

The processes for the preparation of the crude polydispersed oligomers of Formulae I–IV have been described in our copending U.S. patent application Ser. No. 710,370, filed Jun. 10, 1991, the disclosure of which is hereby incorporated by reference.

RESTRICTING THE CRUDE OLIGOMER MIXTURE TO A NARROWER POLYDISPERSED OLIGOMER MIXTURE; STEP 1

Figure 3:
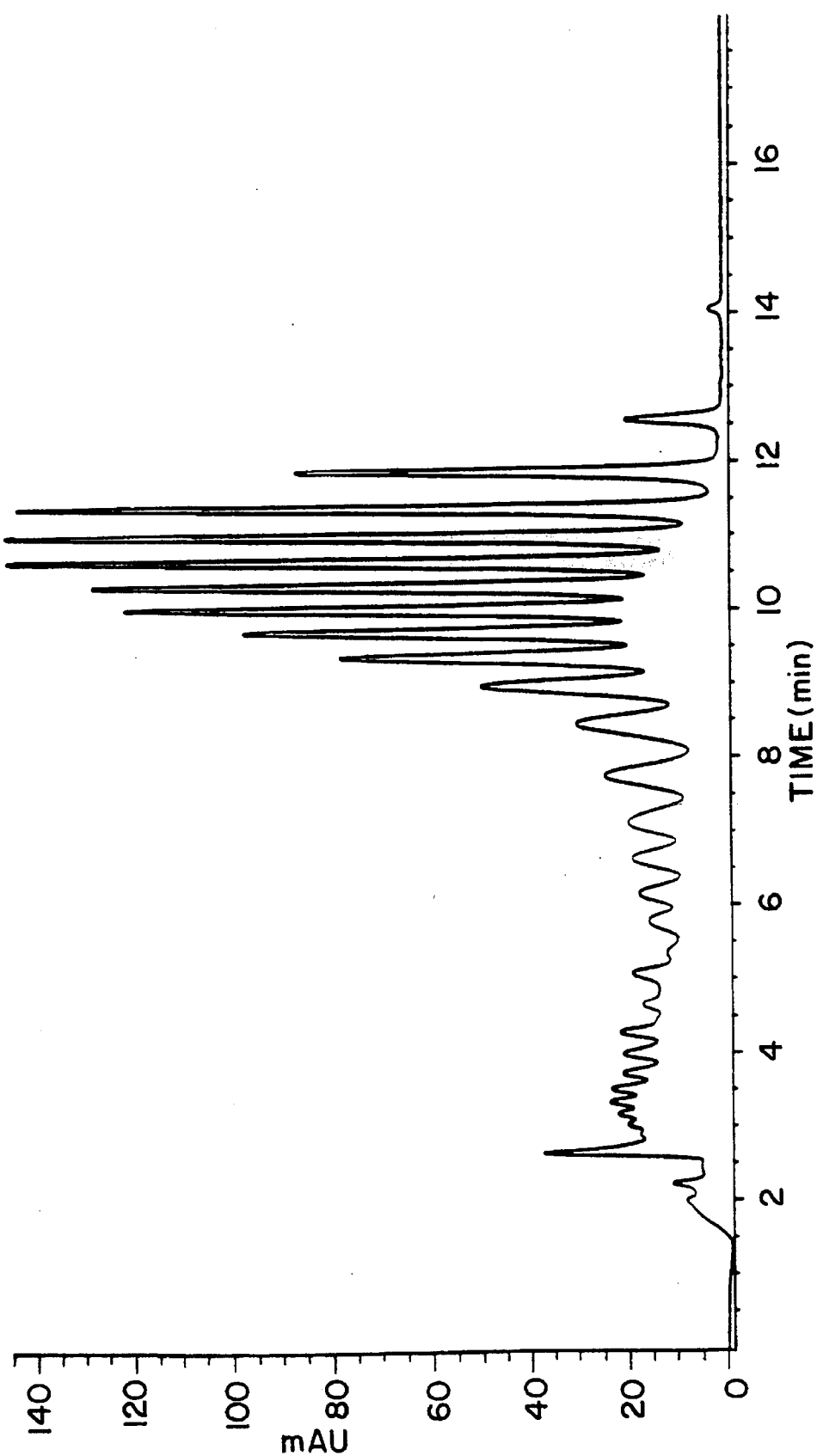

Example 1: Gel Filtration
A:

A solution of 0.542 g in 8.34 mL of water of a crude polydispersed sulfonated polyurea of Formula I, from Example B of the starting materials, with a number average degree of polymerization of 9 (shown by FIG. 1, $M_n$=2348, $M_w$=3408, $M_w/M_n$=1.45) was passed through a gel filtration column. A constant flow of 5.0 mL/min flow of deionized water was maintained using a peristaltic pump. The eluent was monitored at 310 nm by a UV detector for the presence of anionic oligomer mixture. After 40 min the sample began to appear, and 4.0 mL fractions were collected. Analysis by analytical HPLC indicated that the dispersity of each of the fractions was considerably reduced from that of the starting material. For example, fraction 14 (shown by FIG. 2) consisted of 25 mg of a narrow dispersity oligomer ($M_n$=2549, $M_w$=2880, $M_w/M_n$=1.13). Fractions 7 through 17 were combined to give 271 mg of a sample (shown by FIG. 3, $M_n$=2860, $M_w$=3830, $M_w/M_n$=1.34) with a reduced amount of low retention time impurities.

In FIGS. 1–4, the peaks in the time range from 0 to 3 min represents non-capped oligomers, 3 to 5 min represents mono-capped oligomers, 5–14 min represents the desired di-capped oligomers with n=1 at 14 min, n=2 at 13 min. n=3 at 12 min, and similarly counting n from right to left The vertical axis represents UV adsorption at 280 nm in milli-adsorption units ("mAU"). The sample concentration was not determined; therefore the sample to sample peak size variation is not meaningful.
B:

A gel filtration column was prepared by allowing 115 g of Pharmacia Sephadex™ G-10 (40–120 μm bead size) resin to swell in approximately 500 mL of distilled water for one hr. Fines were decanted from the resin mixture after allowing the suspension to settle in a one liter cylinder. A glass column was slurry packed with resin and 500 mL of distilled water were passed through the column resulting in a 2.5×50 cm bed. A constant flow rate was maintained through the column using a peristaltic pump (flow rate about 3 to 4 mL/min). The eluent was monitored at 310 nm by a UV detector for the presence of the narrower polydispersed anionic oligomer mixture product.

A solution of 50 mg of a polydispersed anionic polyurea of Formula I, from Exampl B of the starting materials, with a $M_n$ of 2730, as determined by $^1$H NMR, was dissolved in 2.5 mL of distilled water and applied to the top of the column. The material was eluted with distilled water and three fractions of 25 mL each were collected. Analysis of the fractions by HPLC indicated that fraction 1 was enriched in higher molecular weight oligomers, while fractions 2 and 3 were enriched in lower molecular weight oligomers relative to the starting material.
C:

A solution of crude mixture, 1.078 g in 10 mL of water, of the above prepared bromo end-capped products, from Example A of the starting materials, was passed through a gel filtration column. A constant flow of 5.0 mL/min flow of deionized water was maintained using a peristaltic pump. The eluent was monitored at 310 nm by a UV detector for the presence of oligomer mixture. After 40 min the sample began to appear, and 3.0 mL fractions were collected. Analysis by analytical HPLC indicated that the dispersity of each of the fractions was considerably reduced from that of the starting material. Fractions 8 through 11 were combined to give about 300 mg of a bromo end-capped sample with a reduced amount of low retention time impurities. Thus, a bromo end-capped polydispersed oligomer with improved purity was isolated.

Example 2: Selective Precipitation

A solution of 3.93 g in 40.0 mL of water of a mixture of a crude polydispersed sulfonated polyurea of Formula I, from Example B of the starting materials, with a number average degree of polymerization of 6 was prepared. To this solution was added 40.0 mL of acetone, causing a precipitate which was separated by centrifugation. The soluble portion was evaporated to give 0.82 g of a narrow polydispersity fraction having an average degree of polymerization of about 4.

Example 3: Membrane Permeation

Figure 5:
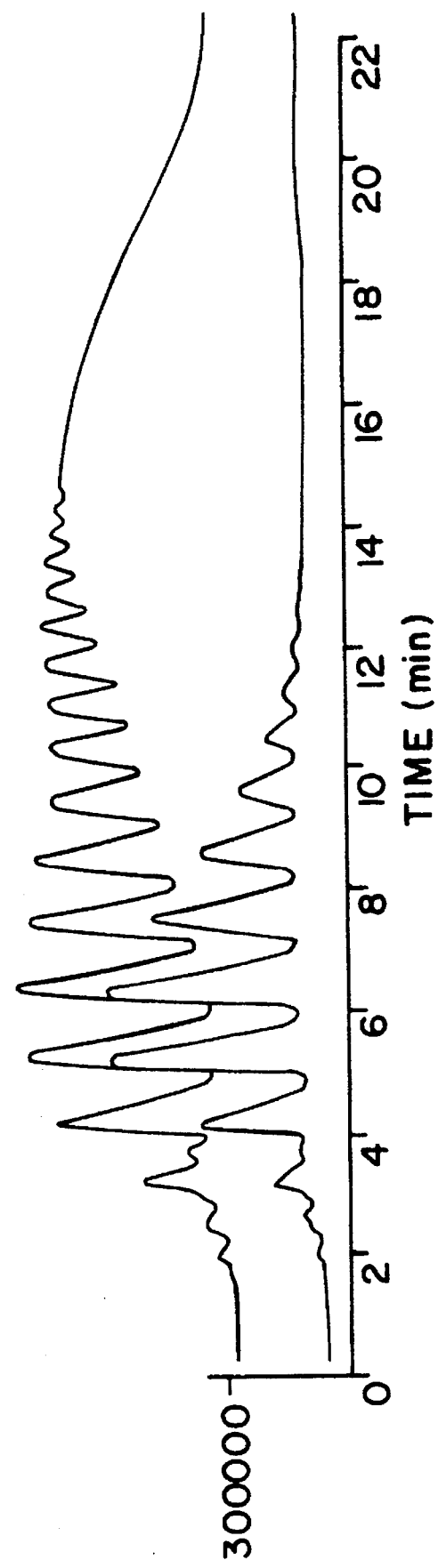

A crude mixture of 167 μL of a 10 mg/mL solution of a polydispersed sulfonated polyurea of Formula I, from Example B of the starting materials, with a number average degree of polymerization of 6 was passed through a membrane filter with a 10,000 Dalton cutoff using a centrifuge. The portion which passed through the filter was similarly fractionated using a membrane with a 3,000 Dalton cutoff. This sequence of separations yields an oligomer mixture in which the dispersity of each of the fractions was considerably reduced from that of the starting material and the low and high molecular portions from the desired degree of polymerization were absent. FIG. 5 shows by the top tracing a crude polydispersed polyurea of Formula I and the second tracing of the material passing through the 10,000 Dalton filter but retained by the 3,000 Dalton filter.

Example 4: Reverse Phase Chromatography

A liquid chromatograph equipped with a diode array detector (280 nm) was modified with a 250 μL sample loop. A reverse phase chromatography column I (9.4 cm×50 mm) filled with 10 μm particles was used. A solution of a crude mixture of 3.8 g in 2.65 mL of water of a polydispersed sulfonated polyurea of Formula I, from Example B of the starting materials, with a number average degree of polymerization of 6 was injected in 200 μL portions. Using a constant ratio of two eluents, 5 mM aqueous (n-Bu$_3$N)PO$_4$ and acetonitrile 45:55 (v/v), a broad peak was observed which was fractionated manually. Each of the fractions were analyzed by HPLC and shown to be mixtures of oligomers with polydispersities narrower than that of the crude starting material.

ISOLATING THE MONODISPERSED OLIGOMER AS ITS AMMONIUM SALT; STEP 2

Example 5: Reverse Phase Chromatography
A:

A liquid chromatograph equipped with a diode array detector (320 nm) was modified with a 250 μL sample loop. A reverse phase chromatography column I (10 mm×250 mm) filled with 3 μm particles was used. A solution of a crude mixture of 905.2 mg in 18.0 mL of water of a polydispersed sulfonated polyurea of Formula I, from Example B of the starting materials, with a number average degree of polymerization of 6 was injected in 200 μL portions. The eluent, pumped at 1.5 mL/min, was a solution of aqueous 5 mM Et$_3$NHOAc, acetonitrile, and tetrahydrofuran. The ratios of the three components were started at 80:20:0 (v/v/v), and linearly changed until at 21.5 min it was 70:30:0 (v/v/v), and linearly changed until at 27 min it was 30:40:30 (v/v/v), which was held constant until 36 min, at which time the run was terminated. After 5 min, an additional sample was injected. The eluent was collected using a fraction collector. After about 24 hrs of continuous elution, the fractions were analyzed. Several fractions containing oligomers (85 to 100 area percent purity) with 2 through 9 repeat units were obtained. These fractions were evaporated at about 20 mm Hg at 50°–55° C. and then dried overnight in a vacuum oven at 50° C. The triethylammonium salts of the polyurea as light amber glasses were obtained in a yield of 10–30 mg.

B:

A liquid chromatograph equipped with a diode array detector (320 nm) was modified with a 250 μL sample loop. A reverse phase chromatography column II (10 mm×250 mm) filled with 3 μm particles was used. A solution of a crude mixture from Example 1C was dissolved in 5 mL of water and filtered. A 75 μL injection size was used. The eluent, pumped at 1.5 mL/min, was a solution of aqueous 50 mM $Et_3NHOAc$ and acetonitrile. The ratios of the two components were started at 70:30 (v/v), remained constant for 10 min, and linearly changed until at 15 min it was 60:40 (v/v), where the ratio was held constant until 25 min, at which time the run was terminated. After 5 min, an additional sample was injected. The eluent was collected using a fraction collector. After about 24 hrs of continuous operation, the fractions were analyzed. Nine fractions containing oligomers (95 to 100 area percent purity) with 1 through 9 repeat units were obtained. These fractions were evaporated at about 20 mm Hg at 50°–55° C. and then dried overnight in a vacuum oven at room temperature. The triethylammonium salts of the monodispersed polyurea $M_w/M_n=$ less than 1.1, as light amber glasses were obtained in a yield of 5–10 mg.

Figure 6:
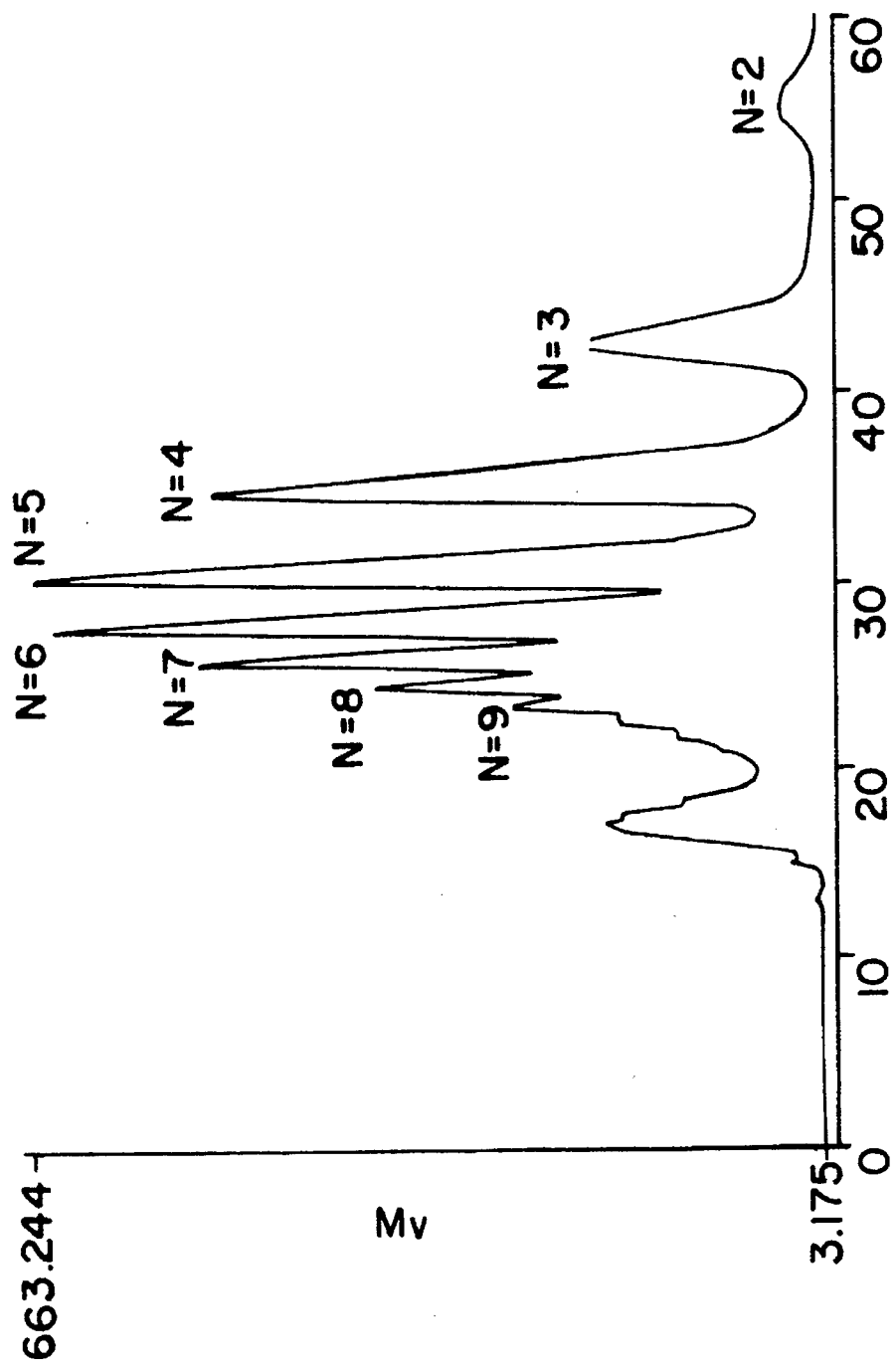
Figure 7:
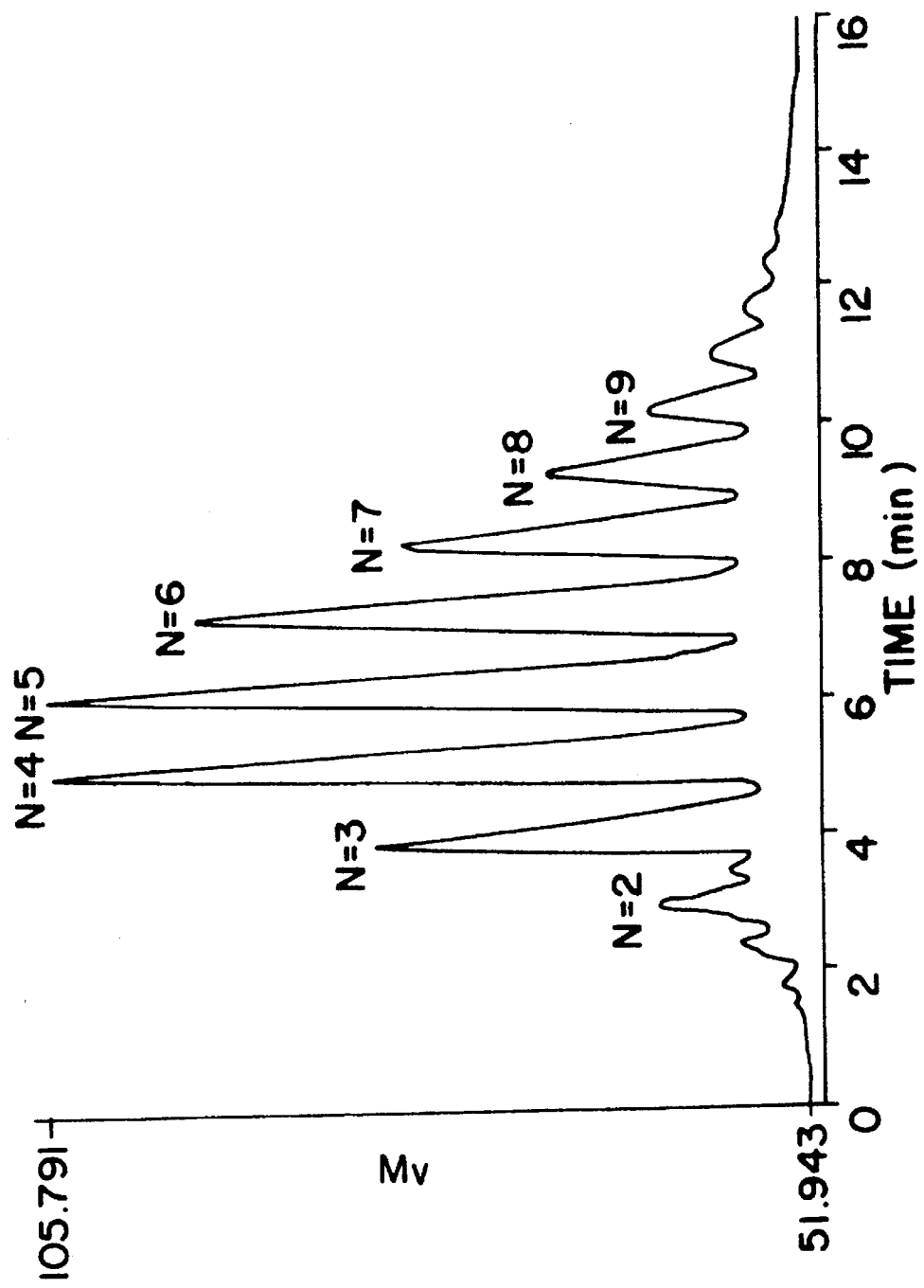
Figure 8:
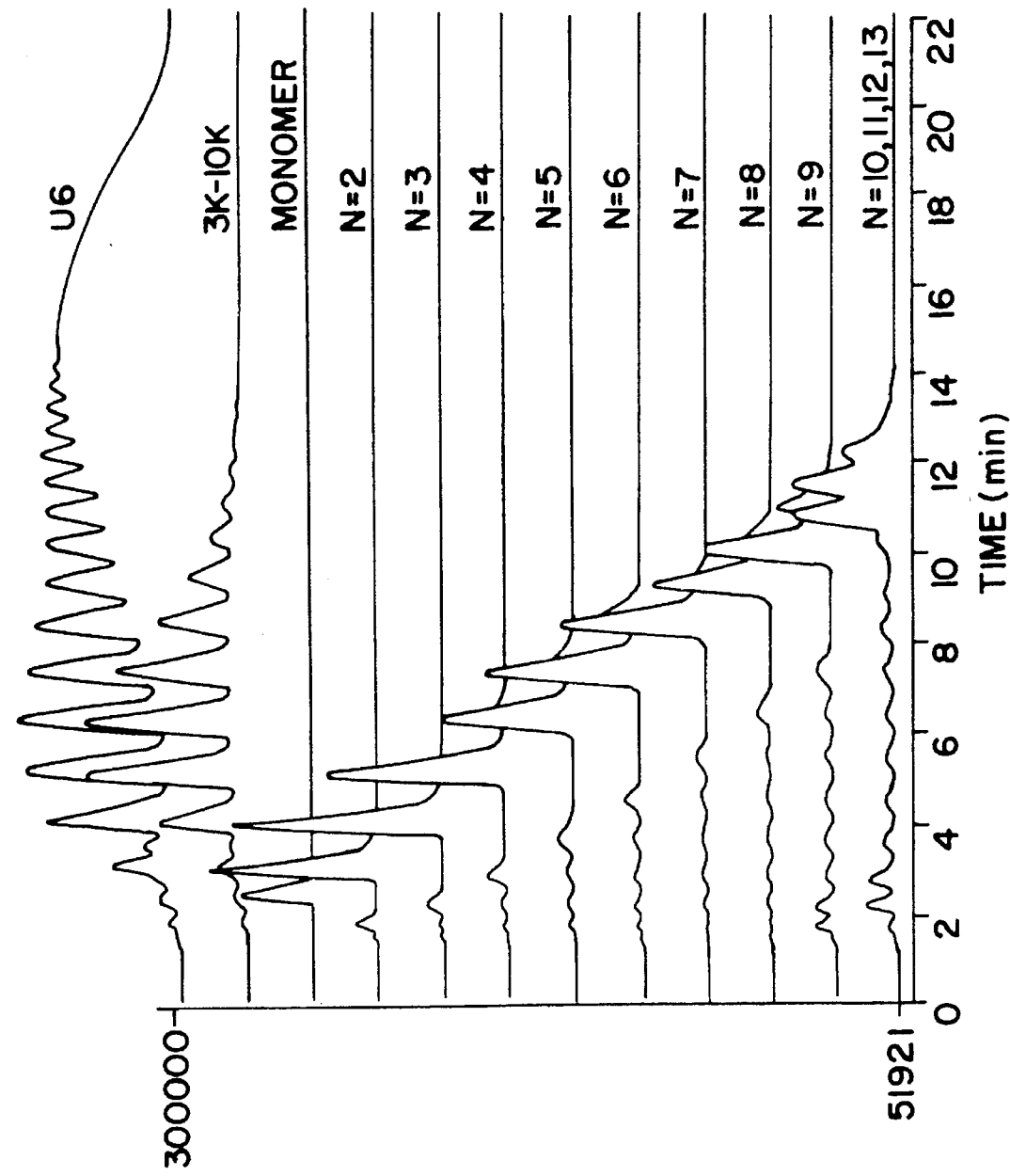

C:

When the separation was run in the presence of $Et_3NHOAc$, the oligomer chain length decreases with increasing retention time; whereas the reverse order of elution was obtained when the separation was conducted in the presence of tetrabutyl ammonium phosphate, i.e. the chain length increases with increasing time. FIG. 6 shows the HPLC profile with $Et_3NHOAc$. FIG. 7 shows the HPLC profile with tetrabutyl ammonium phosphate. FIG. 8 shows an HPLC profile of the purified monodispersed components of FIG. 6.

Other HPLC chromatograms with tetrabutyl ammonium phosphate were run. The various fractions of the oligomers of a polyurea of Formula I are shown in FIG. 8. In FIG. 8 the top tracing represents the starting material of the crude polydispersed oligomer. The chain length of the components increase with increasing retention time (consistent with FIG. 7). The second trace is the oligomer after restricting the crude anionic oligomer mixture to a narrower polydispersed anionic oligomer mixture in the manner of Example 3 by use of membrane filters to restrict the size distribution to the range between 3,000 to 10,000 Daltons. The individual oligomer fractions were collected and then resubjected to HPLC with tetrabutyl ammonium phosphate with the results as shown in the other separate profiles of FIG. 8 where each monodispersed n=1 to 9 is shown. The last profile on FIG. 8 shows an oligomer mixture of n=10 to 13.

CONVERTING THE OLIGOMER AMMONIUM SALT TO THE CORRESPONDING SODIUM SALT; STEP 3

Example 6: Ion Exchange

A:

The samples from Example 5 were individually dissolved in about 2 mL deionized water and passed through syringe cartridge columns which were filled with 0.5 meq of sulfonated crosslinked polystyrene in the acid form. The column was rinsed twice with 1 mL of water. After evaporation, all the samples were analyzed by proton NMR, which showed that the triethylammonium ion had been completely removed and replaced by hydrogen.

Figure 4:
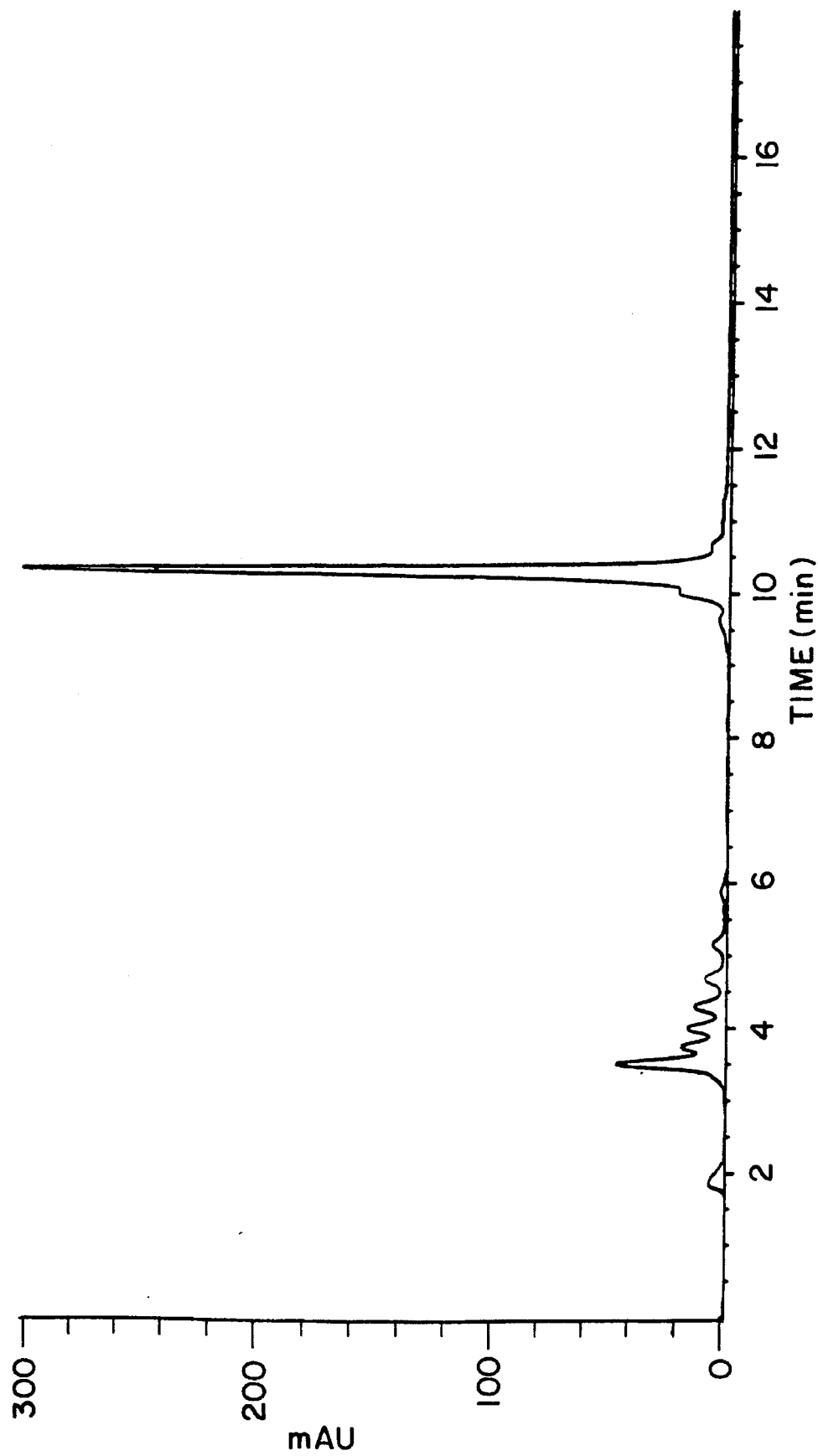

The samples containing oligomers with more than one repeat unit were a mixture of diastereomers. Although these fractions appear to be single compounds, they are actually isomeric mixtures of diastereomers, which is a result of the chiral nature of the biphenyl group in the repeat unit. A typical HPLC analysis is shown by FIG. 4 ($M_w=2950$, $M_n=2800$, $M_w/M_n=1.05$) which shows that a single peak predominates. In this sample the small, early retention time peaks are a mono-capped oligomer series, which results from hydrolysis of the main component during isolation.

The $M_n$ of the oligomers was calculated by comparing the integration of the area of the methyl group on the ends with that of the aromatic region by $^1H$ NMR. Selected samples were also analyzed by time-off-light mass spectroscopy, which confirmed the NMR determination.

B:

Syringe cartridge columns, which were filled with 0.5 meq of sulfonated crosslinked polystyrene in the acid form, were pretreated with 2 mL of 5M NaCl and rinsed with 5 mL of water. The samples from Example 5B were individually dissolved in about 2 mL of deionized water and passed through these columns to exchange the $Et_3NH^+$ cation for $Na^+$. The column was rinsed twice with 1 mL of water. After evaporation, all samples were analyzed by proton NMR, which showed that the triethylammonium ion had been removed. Selected samples were also analyzed by time-of-flight mass spectroscopy, which confirmed the NMR determination.

Example 7: Addition of Salts of Weak, Volatile Acids

Lyophilized polyurea oligomers of Formula I (prepared from BPDS and toluidine and isolated by preparative HPLC using $Et_3NHOAc$ buffer) were dissolved in deionized water and treated with sodium acetate. An equivalent of sodium acetate was added per equivalent of sulfonate in the oligomer. The solution was lypholized for 20 hrs to remove water, triethylamine and acetic acid.

An oligomer fraction of n=9, 63 mg, was dissolved in 10 mL of water and 195 μL of a 1.1M solution of sodium acetate (NaOAc). The solution was lypholized and 57 mg of oligomer was recovered.

In a similar manner an oligomer fraction of n=7, 82 mg, was dissolved in 10 mL of water and 250 μL of a 1.1M solution of NaOAc. The solution was lypholized and 79 mg of oligomer was recovered.

An oligomer fraction of n=5, 162 mg, was dissolved in 10 mL of water and 277 μL of a 1.1M solution of NaOAc. The solution was lypholized and 144 mg of oligomer was recovered.

BIOLOGICAL DATA

Example I: ABILITY OF VARIOUS ANTI-HIV OLIGOMERS TO PREVENT VIRUS-INDUCED CELL DEATH USING MT4 CELLS AND HIV-1 STRAIN RF The antiviral activity of various monodispersed oligomers of a polyurea of Formula I was determined by a standard tetrazolium reduction assay [Nakashima et al., *J. Virol. Methods* 26, 319–330 (1989)]. The oligomers were dissolved in RPMI to a standard concentration (about 100

μg/mL) and were then assayed for anti-HIV activity by making doubling dilutions of the solutions across a 96 well microtitre plate. To each well were then added $5\times10^4$ MT4 cells and 100 TCID50 of virus (HIV-1 strain RF) and the plates incubated at 37° C. for 7 days. MTT was added to each well and the plates incubated for a further 2 hours. The blue formazan crystals were dissolved using acidic isopropanol, and the absorbance measured at 540 nm. The results are given in Table I.

TABLE I

| FRACTION n= | MTT Assay | | |
|---|---|---|---|
| | $M_n$ | $IC_{50}$ μg/mL | $IC_{50}$ μM |
| 2 | 976 | >2 | >24 |
| 3 | 1344 | >2 | >14 |
| 4 | 1712 | >2 | >11.6 |
| 5 | 2080 | 1.8 | 0.86 |
| 6 | 2448 | 0.88 | 0.35 |
| 7 | 2816 | 0.72 | 0.25 |
| 8 | 3184 | 0.7 | 0.21 |
| 9 | 3552 | 0.7 | 0.19 |
| 10–13 | >3920 | 1.7 | ~0.42 |
| poly-dispersed | 2448 | 1.1 | ~0.44 |

Example II: ABILITY TO TREAT CELLS WITH VARIOUS OLIGOMERS AND BLOCK HIV-I INFECTION USING JM CELLS AND GB8 STRAIN OF HIV-I The antiviral activity of various monodispersed oligomers of a polyurea of Formula I was assessed by a standard synctia assay [Cardin et al., Trans. Assoc. Amer. Phys. C, 101–109 (1989) and Cardin et al., J. Biol. Chem. 266, 13355–13363 (1981)]. JM cells were treated at 37° C. with different compounds at various concentrations (μg/mL) or left untreated. The cells in RPMI medium were infected with HIV-I (GB8) for 2 hours at room temperature. The cells were then washed 2 times in RPMI medium and resuspended in fresh medium containing fractionated oligomers prior to being distributed into duplicate wells and incubated at 37° C. After 3 days syncytia were scored. The results are given in Table II.

TABLE II

| FRACTION n= | Synctia Assay | |
|---|---|---|
| | $IC_{50}$ μg/mL | $IC_{50}$ μM |
| 2 | 9 | 9.2 |
| 3 | 7.8 | 5.8 |
| 4 | 1.9 | 1.1 |
| 5 | 0.35 | 0.17 |
| 6 | 0.25 | 0.10 |
| 7 | 0.15 | 0.05 |
| 8 | 0.22 | 0.07 |
| 9 | 0.14 | 0.04 |
| 10–13 | 0.36 | 0.09 |
| poly-dispersed | 0.18 | 0.07 |

FIG. 9 shows a histogram of $IC_{50}$ antivrial concentrations of various oligomer fractions. Antiviral potency increases with increasing oligomer chain length up to n=9. The anti-HIV-1 activity of the polydispersed fraction and the mixture of n=10–13 fraction were approximately equally potent, but both of those fractions were less potent than each n=6 to n=9 fractions of the monodispersed oligomer fractions.

Example I: EFFECT OF A NARROW POLYDISPERSED AND MONODISPERSED POLYUREAS OF FORMULA I ON HSV-2 REPLICATION Vero cells were grown to confluency in 24 well tissue culture plates. The cells were infected with HSV-2 at a multiplicity of infection of 50-pfu/well. The infection was carried out either in the presence or absence of different concentrations of a compound which is BPDS/P/T, and named as poly{imino[2,2'-disulfo(1,1'-biphenyl)- 4,4'-diyl] iminoearbonyl}, alpha-{[(4-methylphenyl)amino] -carbonyl}-omega-[(4-methylphenyl)amino] - and is represented by Formula I in claim 1 when R is 4-methylphenyl, $R^2$ is hydrogen, X is

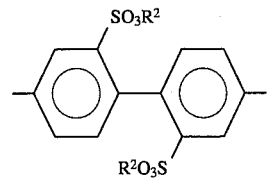

and n is defined as stated in Table I. After a 2 hour absorption at room temperature, the inoculum was removed and the cells incubated with an agarose overlay containing the appropriate concentration of compound. After 2 days at 37° C. the cells were fixed and stained with methylene blue. The plaques were counted and the percentage inhibition calculated for each concentration of compound. The $IC_{50}$ for each compound was calculated using linear regression analysis and the results are given in Table I.

TABLE III

| Herpes Simplex Type II | |
|---|---|
| FRACTION n= | $IC_{50}$ μg/mL |
| 2 | >10 |
| 3 | <10 |
| 4 | <10 |
| 5 | <10 |
| 6 | <1 |
| 7 | <1 |
| 8 | <1 |
| 9 | <1 |
| 10–13 | <1 |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A process for the preparation of narrow polydispersed anionic oligomers, having a polydispersity ratio of 1.0 to 1.3, which are water-soluble oligomers comprising 3 to 50 recurring units coupled by carbonyl linking moieties, said oligomer having anionic groups and predominantly linear geometry such that regular spacing between anionic groups exists in an aqueous medium, and which are represented by any one of the following formulae:

A) polyureas of the formula:

$$R\text{---}\left[\overset{H}{\underset{}{N}}\text{---}\underset{\underset{O}{\|}}{C}\right]_m\left[\overset{H}{\underset{}{N}}\text{---}X\text{---}\overset{H}{\underset{}{N}}\text{---}\overset{O}{\underset{}{\overset{\|}{C}}}\right]_n\overset{H}{\underset{}{N}}\text{---}R^3 \qquad I$$

wherein:

R represents hydrogen, $C_{1-20}$ alkyl, phenyl, or phenyl substituted with from 1 to 2 —$SO_3R^2$ moieties and up to 3 substituents independently selected from chloro, bromo or $C_{1-4}$ alkyl;

$R^2$ represents hydrogen or a pharmaceutically acceptable cation;

m is 0 or 1, with the proviso that when m is 0, R is hydrogen;

X represents:

[chemical structures showing various substituted aromatic rings with $SO_3R^2$ and $R^2O_3S$ groups]

n is 3–50; and $R^3$ represents —R or —X—$NH_2$ where R and X are defined as before;

B) polycarbonates of the formula:

$$X^1\text{---}O\text{---}\left[\overset{O}{\underset{}{\overset{\|}{C}}}\text{---}O\text{---}X\text{---}O\right]_n\text{---}X^2 \qquad II$$

wherein:

X and n are defined as in Formula I above;

$X^1$ represents HO—X—, wherein X is defined as in Formula I above, $C_{1-20}$ alkyl, phenyl or phenyl substituted with from 1 to 2 —$SO_3R^2$ moieties and up to 3 substituents independently selected from chloro, bromo or $C_{1-20}$ alkyl; and $X^2$ represents hydrogen or —$CO_2X^1$, wherein $X^1$ is defined as above;

C) polyesters of the formula:

$$R^4\text{---}O\text{---}\left[\overset{O}{\underset{}{\overset{\|}{C}}}\text{---}X_3\text{---}\overset{O}{\underset{}{\overset{\|}{C}}}\text{---}O\text{---}X\text{---}O\right]_n\text{---}R^5 \qquad III$$

wherein:

X and n are defined as in Formula 1 above;

$R^4$ represents —$R^2$, as defined above in Formula 1, or —$X^1$, as defined above in Formula II;

$R^5$ represents:

$$R^4\text{---}O\text{---}\overset{O}{\underset{}{\overset{\|}{C}}}\text{---}X_3\text{---}\overset{O}{\underset{}{\overset{\|}{C}}}\text{---}$$

wherein $R^4$ is defined above as in Formula III above, or —$R^2$ as defined in above Formula I;

$X^3$ represents:

[chemical structures showing various substituted aromatic and biphenyl rings with $SO_3R^2$ and $R^2O_3S$ groups]

D) polyamides of the formula:

$$R^6\text{---}\left[\overset{O}{\underset{}{\overset{\|}{C}}}\text{---}X^3\text{---}\overset{O}{\underset{}{\overset{\|}{C}}}\text{---}\underset{\underset{H}{|}}{N}\text{---}X\text{---}\underset{\underset{H}{|}}{N}\right]_n\text{---}R^7 \qquad IV$$

wherein:

X and n are defined as above in Formula I;

$X^3$ is defined as above in Formula III;

$R^6$ represents $H_2N$—X—NH—, $R^2O$—, RNH— or R—C(O)—NH—X—NH—, where R, $R^2$ and X are defined above as in Formula I;

$R^7$ represents hydrogen, $$R_2O\text{---}\overset{O}{\underset{}{\overset{\|}{C}}}\text{---}X_3\text{---}\overset{O}{\underset{}{\overset{\|}{C}}}\text{---}; \quad R\text{---}\overset{O}{\underset{}{\overset{\|}{C}}}\text{---} \quad \text{or} \quad RNH\text{---}\overset{O}{\underset{}{\overset{\|}{C}}}\text{---}X_3\text{---}\overset{O}{\underset{}{\overset{\|}{C}}}\text{---}$$

wherein R and $R^2$ are defined as above in Formula I, and $X^3$ is defined above as in Formula III, which comprises the steps of:

1) restricting a crude polydispersed anionic oligomer mixture, having a polydispersity ratio>1.3, containing oligomers of one of Formulas I–IV to a narrow polydispersed anionic oligomer mixture, wherein the manner of restricting is chosen from a group consisting of gel filtration, membrane permeation and reverse phase chromatography; optionally followed by;

2) isolating a monodispersed anionic oligomer mixture; and 3) optionally converting the narrow polydispersed or monodispersed anionic oligomer mixtures from step 1) or 2) into a desired pharmaceutically-acceptable salt.

2. The process according to claim 1 wherein the prepared oligomer is a polyurea of Formula I and is monodispersed, having a polydispersity ratio of 1.0 to 1.15 wherein n is from 3 to 15.

3. The process according to claim 2 wherein n is from 5 to 10.

4. The process according to claim 2 wherein n is from 6 to 9.

5. The process according to claim 1 wherein the optionally prepared pharmaceutically acceptable salt prepared in Step 3 is an ammonium salt.

6. The process according to claim 1 wherein the optionally prepared pharmaceutically acceptable salt prepared in Step 3 is a sodium salt.

7. The process according to claim 1 wherein the optionally prepared pharmaceutically acceptable salt prepared in Step 3 is a potassium salt.

8. The process according to claim 1 wherein Step 1 is accomplished by gel filtration.

9. The process according to claim 1 wherein Step 1 is accomplished by membrane permeation.

10. The process according to claim 1 wherein Step 1 is accomplished by reverse phase chromatography.

11. The process according to claim 1 wherein Step 2 is accomplished by reverse phase chromatography.

12. The process according to claim 1 wherein Step 2 is accomplished by gel electrophoresis.

13. The process according to claim 1 wherein Step 3 is accomplished by ion exchange.

14. The process according to claim 1 wherein Step 3 is accomplished by addition of a salt of a weak, volatile acid.

15. The process according to claim 2 wherein the purity of the monodispersed oligomers is at least 75%.

16. The process according to claim 15 wherein the purity of the monodispersed oligomers is from about 85% to about 100%.

17. The process according to claim 1 wherein the polydispersity ratio of the narrow polydispersed oligomers is from 1.0 to 1.2.

18. The process according to claim 17 wherein the polydispersity ratio is from 1.0 to 1.15.

19. The process according to claim 1, wherein the oligomers are monodispersed, having a polydispersity ratio from 1.0 to 1.1.

20. The process according to claim 1 wherein the prepared oligomer is a polyurea of Formula I wherein the polydispersity ratio is from 1.0 to 1.2 and n is from 3 to 15.

21. The process of claim 20 wherein the polydispersity ratio is from 1.0 to 1.15.

22. The process of claim 21 wherein the oligomer polydispersity ratio is from 1.0 to 1.1.

* * * * *

UNITED STATES PATENT AND TRADEMARK OFFICE
CERTIFICATE OF CORRECTION

PATENT NO. : 5,512,177

DATED : April 30, 1996

INVENTOR(S) : Alan D. Cardin, et al.

It is certified that error appears in the above-identified patent and that said Letters Patent is hereby corrected as shown below:

At column 2, line 59, the patent reads "abdoman" and should read --abdomen--.
At column 2, line 67, the patent reads "vital" and should read --viral--.
At column 3, line 11, the patent reads "negligable" and should read --negligible--.
At column 4, line 54, the patent reads "ranger" and should read --range,--.
At column 4, line 58, and again at column 5, line 7, the patent reads "horizonal" and should read --horizontal--.
At column 6, line 20, the patent reads "SO$_3$R$_2$" and should read --SO$_3$R$^2$--.
At column 12, line 50, and again at line 51, the patent reads "4methylphenyl" and should read --4-methylphenyl--.
At column 13, line 54, the patent reads "4phenylene" and should read --4-phenylene--.
At column 21, line 27, the patent reads "who as" and should read --who has--.
At column 21, line 38, the patent reads "cultrue" and should read --culture--.
At column 21, line 57, the patent reads "by either by" and should read --either by--.
At column 25, line 52, the patent reads "Exampl" and should read --Example--.
At column 30, line 11, the patent reads "iminoearbonyl" and should read --iminocarbonyl--

Signed and Sealed this

Seventh Day of April, 1998

Attest:

BRUCE LEHMAN

Attesting Officer

Commissioner of Patents and Trademarks